US010932305B2

(12) United States Patent
Zeilingold et al.

(10) Patent No.: US 10,932,305 B2
(45) Date of Patent: Feb. 23, 2021

(54) DYNAMIC PROVISIONING OF WIRELESS DEVICES WITH HEALTH GATEWAYS

(71) Applicant: PHILIPS HEALTHCARE INFORMATICS, INC., Cambridge, MA (US)

(72) Inventors: Daphna Zeilingold, San Diego, CA (US); Robert Ganton, San Diego, CA (US); Soumya Das, San Diego, CA (US); Ashutosh Aggarwal, San Diego, CA (US); John Earl Amschler, Del Mar, CA (US)

(73) Assignee: Koninklijke Philips N.V., Eindhoven (NL)

( * ) Notice: Subject to any disclaimer, the term of this patent is extended or adjusted under 35 U.S.C. 154(b) by 0 days.

(21) Appl. No.: 15/996,245

(22) Filed: Jun. 1, 2018

(65) Prior Publication Data
US 2018/0368197 A1     Dec. 20, 2018

Related U.S. Application Data

(60) Provisional application No. 62/520,360, filed on Jun. 15, 2017.

(51) Int. Cl.
*H04B 7/00*     (2006.01)
*H04W 76/11*    (2018.01)
(Continued)

(52) U.S. Cl.
CPC ............ *H04W 76/11* (2018.02); *G16H 10/60* (2018.01); *G16H 20/40* (2018.01); *G16H 40/63* (2018.01);
(Continued)

(58) Field of Classification Search
CPC ..... H04W 76/11; H04W 8/005; H04W 88/16; G16H 40/67; G16H 10/60
(Continued)

(56) References Cited

U.S. PATENT DOCUMENTS

2011/0137681 A1*  6/2011  Lim ................. G16H 10/60
                                                       705/3
2011/0268047 A1* 11/2011  Nath ................. H04W 8/186
                                                       370/329
(Continued)

FOREIGN PATENT DOCUMENTS

WO     2013140253 A1    9/2013

OTHER PUBLICATIONS

International Search Report and Written Opinion—PCT/US2018/035832—ISA/EPO—dated Aug. 23, 2018.
(Continued)

*Primary Examiner* — Kathy W Wang-Hurst
*Assistant Examiner* — Max Mathew

(57) ABSTRACT

Example systems, methods, computer-readable media, and apparatuses for dynamic provisioning of wireless devices with health gateways are disclosed. One example method includes detecting, by a wireless device, a signal from a health gateway, the signal including connection information and service information; determining whether the health gateway is a suitable based on the connection information and the service information; and in response to determining that the health gateway is suitable, establishing a communications connection with the health gateway.

31 Claims, 14 Drawing Sheets

(51) Int. Cl.
*H04W 48/18* (2009.01)
*G16H 40/63* (2018.01)
*G16H 50/30* (2018.01)
*G16H 20/40* (2018.01)
*G16H 40/67* (2018.01)
*G16H 10/60* (2018.01)
*H04W 8/00* (2009.01)
*H04W 88/16* (2009.01)

(52) U.S. Cl.
CPC ............. *G16H 40/67* (2018.01); *G16H 50/30* (2018.01); *H04W 8/005* (2013.01); *H04W 48/18* (2013.01); *H04W 88/16* (2013.01)

(58) Field of Classification Search
USPC ................................................. 455/41.1, 41.2
See application file for complete search history.

(56) References Cited

U.S. PATENT DOCUMENTS

| | | | | |
|---|---|---|---|---|
| 2012/0293322 | A1* | 11/2012 | Ray | H04L 67/327 340/539.12 |
| 2013/0162160 | A1* | 6/2013 | Ganton | H05B 47/10 315/210 |
| 2014/0379368 | A1* | 12/2014 | Kim | G16H 10/60 705/2 |
| 2016/0019499 | A1 | 1/2016 | Bhalodia et al. | |
| 2016/0042483 | A1* | 2/2016 | Vo | G06Q 50/24 705/3 |
| 2016/0210429 | A1 | 7/2016 | Ortiz et al. | |
| 2016/0314452 | A1* | 10/2016 | Pochic | G06Q 20/027 |
| 2016/0339190 | A1 | 11/2016 | Morrison et al. | |
| 2017/0177817 | A1* | 6/2017 | Loose | G06F 19/00 |
| 2018/0124249 | A1* | 5/2018 | Hassan | H04L 12/1818 |
| 2019/0052745 | A1* | 2/2019 | Wu | H04M 1/72533 |

OTHER PUBLICATIONS

Moosavi S.R., et al., "SEA: A Secure and Efficient Authentication and Authorization Architecture for IoT-Based Healthcare Using Smart Gateways", Procedia Computer Science, vol. 52, Jan. 1, 2015, XP055498924, Amsterdam, NL, ISSN: 1877-0509, DOI: 10.1016/j.proc s.2015.05.013, pp. 452-459.
International Application No. PCT/US2018/035832, International Preliminary Report on Patentability dated Dec. 26, 2019, 12 pages.

* cited by examiner

AD Structure 1 — 600

| Field Name | Length in Octets | Description and Value |
|---|---|---|
| Length | 1 | Length (in octets) of the AD data. E.g., 0x02 |
| AD Type | 1 | Advertisement type is Flags. E.g., 0x01 |
| Flags | 1 | Bit 1 (LE General Discoverable Mode) and Bit 2 (BR/EDR not supported) |

AD Structure 2 — 610

| Field Name | Length in Octets | Description and Value |
|---|---|---|
| Length | 1 | Length (in octets) of the AD data. E.g., 0x03 |
| AD Type | 1 | Advertisement type is incomplete list of 16-bit service UUIDs. E.g., 0x02 |
| Flags | 1 | 16 bit service UUID |

AD Structure 3 — 620

| Field Name | Length in Octets | Description and Value |
|---|---|---|
| Length | 1 | Length (in octets) of the AD data. E.g., 0x09 |
| AD Type | 1 | Advertisement type is Manufacturer-Specific Data ("MSD"). E.g., 0xFF |
| Company ID | 2 | Company ID Code |
| MSD Format | 1 | MSD Version |
| PRN | 1 | Pseudo-random number that changes periodically to ensure that new advertisement data is unique, which may bypass some filtering techniques used by aggressive host devices |
| Device Model ID | 2 | Unique model ID assigned by the manufacturer for the type of device |
| Passcode | 3 | e.g., Hex-encoded ASCII with 6 digits represented |

*FIG. 6B*

| Field Name | Length in Octets | Description and Value |
|---|---|---|
| Length | 1 | Length (in octets) of the AD data. E.g. 0x03 |
| AD Type | 1 | Advertisement type is Manufacturer Specific Data ("MSD"). |
| Company ID | 2 | Company identifier value. |
| MSD Format | 1 | MSD version number |
| PRN | 1 | Pseudo-random number ("PRN") subject to periodic change |
| Device Model ID | 2 | Unique model ID assigned by company |

AD Structure 3A
730

*FIG. 7B*

DYNAMIC PROVISIONING OF WIRELESS DEVICES WITH HEALTH GATEWAYS

CROSS-REFERENCE TO RELATED APPLICATIONS

This application claims the benefit of U.S. Provisional Application No. 62/520,360, filed Jun. 15, 2017, entitled "Dynamic Provisioning of Wireless Devices with Health Gateways" which is incorporated herein by reference.

BACKGROUND

Patients using medical devices may periodically obtain information from such devices, such as blood pressure, heart rate, etc., and record it as a part of a treatment plan from a health care provider, or in the course of post-procedure (e.g., post-surgery) monitoring. In some examples, the patient may use an electronic device, such as a smartphone, to record such information to later provide to their health care provider. Such information may help the health care provider determine whether a patient is responding to treatment or is recovering appropriately from surgery.

BRIEF SUMMARY

Various examples are described for dynamic provisioning of wireless devices with health gateways. One example method includes detecting, by a wireless device, a signal from a health gateway, the signal including connection information and service information; determining whether the health gateway is a suitable based on the connection information and the service information; and in response to determining that the health gateway is suitable, establishing a communications connection with the health gateway.

An example wireless device includes a wireless transceiver; a non-transitory computer-readable medium; and a processor in communication with the non-transitory computer-readable medium and configured to: detect, using the wireless transceiver, a signal from a health gateway, the signal including connection information and service information; determine whether the health gateway is a suitable based on the connection information and the service information; and in response to a determination that the health gateway is suitable, establish a communications connection with the health gateway.

One example non-transitory computer-readable medium includes processor-executable instructions configured to cause a processor to detect, by a wireless device, a signal from a health gateway, the signal including connection information and service information; determine whether the health gateway is a suitable based on the connection information and the service information; and in response to a determination that the health gateway is suitable, establish a communications connection with the health gateway.

Another example method includes receiving a wireless signal from a wireless device, the wireless signal indicating information about the wireless device; determining whether the wireless device is suitable based on the information about the device; and in response to a determination that the wireless device is suitable, establishing a communications connection with the wireless device.

Another example wireless device includes a wireless transceiver; a non-transitory computer-readable medium; and a processor in communication with the non-transitory computer-readable medium and configured to receive, using the wireless transceiver, a wireless signal from a wireless device, the wireless signal indicating information about the wireless device; determine whether the wireless device is suitable based on the information about the device; and in response to a determination that the wireless device is suitable, establish a communications connection with the wireless device.

A further example method includes transmitting, by a wireless medical device, an advertisement packet; receiving a wireless signal from a health gateway, the wireless signal indicating the wireless medical device is suitable to connect with the health gateway; and in response to receiving the wireless signal, establishing a communications connection with the health gateway.

These illustrative examples are mentioned not to limit or define the scope of this disclosure, but rather to provide examples to aid understanding thereof. Illustrative examples are discussed in the Detailed Description, which provides further description. Advantages offered by various examples may be further understood by examining this specification

BRIEF DESCRIPTION OF THE DRAWINGS

The accompanying drawings, which are incorporated into and constitute a part of this specification, illustrate one or more certain examples and, together with the description of the example, serve to explain the principles and implementations of the certain examples.

FIGS. 6A-6B shows an example packet format for dynamic provisioning of wireless devices with health gateways;

FIGS. 7A-7B shows an example packet format for dynamic provisioning of wireless devices with health gateways;

DETAILED DESCRIPTION

Figure 1A:
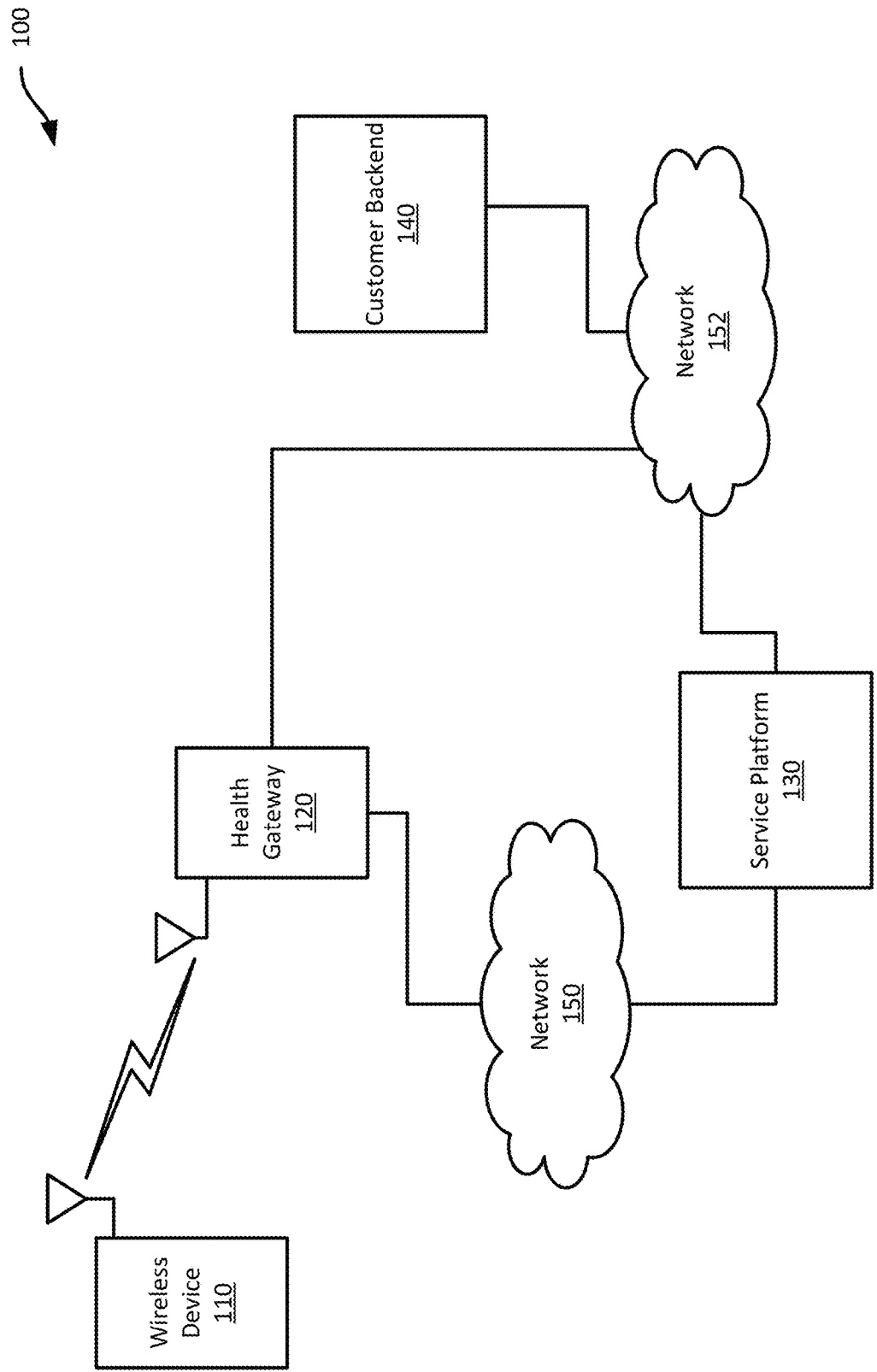
FIGS. 1A-1B show example systems for dynamic provisioning of wireless devices with health gateways.

Examples are described herein in the context of dynamic provisioning of wireless devices with health gateways. Those of ordinary skill in the art will realize that the following description is illustrative only and is not intended to be in any way limiting. Reference will now be made in detail to implementations of examples as illustrated in the accompanying drawings. The same reference indicators will be used throughout the drawings and the following description to refer to the same or like items.

In the interest of clarity, not all of the routine features of the examples described herein are shown and described. It will, of course, be appreciated that in the development of any such actual implementation, numerous implementation-specific decisions must be made in order to achieve the developer's specific goals, such as compliance with application- and business-related constraints, and that these specific goals will vary from one implementation to another and from one developer to another.

To obtain or provide health monitoring or other related services, a health gateway may be installed at a location, such as a private residence, group home, hospital, etc., in which one or more persons may be monitored, such as via medical devices used by, worn on, or implanted in the person. The health gateway may communicate with and receive data from these medical devices and provide that data to a cloud service provider associated with the health gateway. The data may then be provided to a health care provider or other service provider associated with the persons being monitored.

In some examples, a medical device may be one that is used over a long period of time, e.g., one or more years. However, others may have relatively short life spans, e.g., days or weeks, and thus may be disposable or replaced frequently. Such devices may include inhalers, battery-powered patches, etc. Because of their disposable nature, it may be difficult to pre-authorize, or pre-provision, the health gateway to recognize and communicate with each of these devices. Instead, examples according to this disclosure may allow a health gateway to dynamically recognize and provision a wireless medical (or other) device for use with the health gateway without the patient manually provisioning the device, e.g., by manually entering device information onto the health gateway. After the device(s) have been provisioned, the health gateway can obtain data from the device(s) and provide it to the cloud service provider, which can, if appropriate, provide the data to a health care provider associated with the individual using the medical (or other) device.

In one illustrative example, a patient buys a new inhaler to help with the patient's asthma symptoms. The inhaler includes a small battery-powered Bluetooth Low Energy ("BLE") device that tracks usage of the inhaler and can wirelessly transmit the usage data to a health gateway. After removing the inhaler from the box, the patient presses a button on the inhaler to activate it for use, which in turn activates the wireless device. The wireless device then begins to broadcast BLE packets to identify a nearby health gateway.

In this example, the patient's health gateway receives one of the broadcast packets from the inhaler and extracts information from the packet that includes information about the device, such as a universally-unique identifier ("UUID"), manufacturer-specific data, a company or service provider ID, a model ID, and connection information, such as a passcode, internet protocol ("IP") address, BLE identifier, service set identifier ("SSID"), or other information usable to establish a communications connection between the wireless device and the health gateway. The health gateway then examines the extracted data to determine whether the device is of a type that it should communicate with. For example, the inhaler may transmit its UUID, a manufacturer ID, an ID for the patient's health care provider that prescribed the inhaler, the model of the inhaler, and the inhaler's BLE passcode. The health gateway may then compare the received information with known manufacturers, inhaler models, and determine whether the health gateway is registered with the identified health care provider. If each of the comparisons is validated, the health gateway may then establish a BLE connection with the inhaler using the passcode. After connecting with the inhaler, the health gateway may then obtain data from the inhaler, such as usage data, expiration information, refill information, reordering information, etc. The obtained information is then sent to a cloud service provider that services the health gateway, and relevant information is then also forwarded to one or more of the patient's healthcare providers, e.g., a doctor's office, hospital, or insurance company.

This illustrative example is given to introduce the reader to the general subject matter discussed herein and the disclosure is not limited to this example. The following sections describe various additional non-limiting examples and examples of systems and methods for dynamic provisioning of wireless devices with health gateways.

Referring now to FIG. 1A, FIG. 1A shows an example system 100 for dynamic provisioning of wireless devices with health gateways. The system 100 includes a wireless device 110 and a health gateway 120 that are able to communicate wirelessly with each other. The health gateway 120 is connected via a network 150 to service platform 130, which is connected via network 152 to a customer backend 140. In this example, the wireless device 110 and the health gateway 120 communicate directly with each other over a wireless medium; however, in some examples, the wireless device 110 and health gateway 120 may communicate using intermediary devices, such as in a mesh networking environment where the wireless device 110 communicates with an access point that then communicates with the health gateway 120 over a network infrastructure. Still other indirect communication techniques may be employed as well, such as WiFi repeaters or through a WiFi access point ("AP").

The wireless device 110 in this example system 100 is a disposable medical device, such as an inhaler, an injector device (e.g., an EpiPen®), biometric sensor, etc. Examples according to this disclosure may be suitable for use with disposable medical devices because a patient may frequently obtain replacements that will not be recognized by the health gateway 120. However, examples according to this disclosure may enable such devices to connect to and provide information to the health gateway 120. In addition, while long-term patient devices, such as fitness trackers, insulin pumps, etc., that are replaced less frequently and may be more suitable to be pre-provisioned with a health gateway 120 by its manufacturer due, examples according to this disclosure may be employed with such devices as well.

Provisioning generally relates to establishing and storing identity information for an authorized device with the health gateway, e.g., on the health gateway 120 or the service platform 130, to instruct the health gateway that it is both authorized to communicate with and for which data should be obtained and communicated to the service platform 130 and potentially on to the customer backend 140. For long-term-use devices such as fitness trackers, pre-provisioning may be desirable because it may only be needed once or a small number of times, as such devices typically have useful lifetimes measured in years. Such pre-provisioning of long-term-use devices may be done at the time the health gateway 120 is manufactured or via software or firmware updates pushed to the health gateway 120, such as by the service platform 130 or the customer backend 140. The pre-provisioning may provide information about wireless devices that are authorized to communicate with the health gateway 120. In some examples, wireless device provisioning may be performed manually by the patient by interacting with the health gateway 120, e.g., via a web page, to register and provision the device. Such provisioning may provide information about the device, such as a media access control ("MAC") ID or other UUID, and connection information, including access credentials, such as a passcode, patient name, password, etc., that will enable the health gateway 120 to recognize a wireless device and allow a wireless connection to be established between the two.

In one example, the health gateway 120 is a computing device that includes wireless AP functionality as well as connectivity via either or both networks 150, 152 to the service platform 130 and the customer backend 140. The health gateway 120 provides data collection from connected wireless devices as well as interface functionality between provisioned wireless devices and the service platform 130 and customer backend 140. Health gateways 120 may be installed in any suitable location, such as in a patient's personal residence, within a group residential area, such as in a retirement home or assisted living environment, or in a health care facility, such as a hospital, clinic, or hospice or end-of-life facility.

In some examples, the health gateway 120 may be provided by a software application executed by a processor or chipset of a wireless device, such as a wireless AP. Such a wireless AP may provide other features, such as general network connectivity, media servers, virus or intrusion detection, etc. In some examples, the health gateway 120 may be an electronic accessory, e.g., a dongle, that can be plugged into a port in an access point, such as a Universal Serial Bus ("USB") port. The wireless device 110 may then communicate with the health gateway 120 using the wireless AP as an intermediary, while the health gateway 120 employs the network connectivity provided by the wireless AP to access one or more external networks, e.g., networks 150, 152. In some examples, the health gateway 120 may be a wireless AP that lacks its own direct connection to an external network, and thus it may further communicate with another AP using either a wired or wireless connection.

For example, the health gateway 120 may periodically obtain data from connected wireless device 110 by polling the devices or receiving scheduled data downloads from the devices. The data obtained from the wireless devices may be stored locally on the health gateway 120 or may be transferred to the service platform 130 or customer backend 140.

As an interface to the service platform 130 or customer backend 140, the health gateway 120 provides data obtained from provisioned wireless devices, e.g., wireless device 110, to the service platform 130 or the customer backend 140, and may receive information from either or both. For example, the health gateway 120 may receive software updates or firmware updates for the health gateway 120 itself or for one or more of the wireless devices 110. The health gateway 120 may receive new or updated information about authorized device types, authorized service providers, authorized device manufacturers, data polling or upload periods, data types, etc. In some examples the health gateway 120 may receive alerts, coupons, notifications, recall information, warnings, etc., from either or both of the service platform 130 or the customer backend 140. Such information may be provided to a patient via one or more of the wireless devices 110 or via another avenue such as an email, text message, or a spoken message delivered by a speaker on the health gateway 120.

In this example, the service platform 130 provides storage and management features for the health gateway 120. For example, the service platform 130 may include a cloud storage location for data obtained by the health gateway 120 from one or more wireless device 110. The service platform 130 may also provide access to a patient via a web page that may enable the patient to modify account settings, health gateway settings, pre-provision devices for use with one or more health gateways 120, settings or accounts with one or more customer backends 140, etc. The service platform 130 may also communicate with one or more customer backends 140 via a network 152, such as to provide data obtained from one or more wireless devices 110 to one or more customer backends 140.

In this example, the customer backend 140 is a system that is operated by a health care provider used by the patient, such as a doctor's office, hospital, rehabilitation clinic, insurance company, etc. The customer backend 140 can receive data from one or more of the patient's wireless devices 110 and store the data or process the data and act upon it. For example, the customer backend 140 may be able to detect a need for a prescription refill, a need to reorder a disposable wireless device (e.g., an inhaler is down to 25 percent capacity), or potential medical conditions, such as drug side effects, an increase in asthma attacks, low blood pressure, etc.

The customer backend 140 may also send information or notifications to the patient via multiple different routes. For example, the customer backend 140 may send information or notifications to the service platform 130, which may in turn provide them to the health gateway 120 and to the wireless device 110. In some examples, the customer backend 140 may instead send an email or text message to the patient via a register cellular number or email address.

Figure 1B:
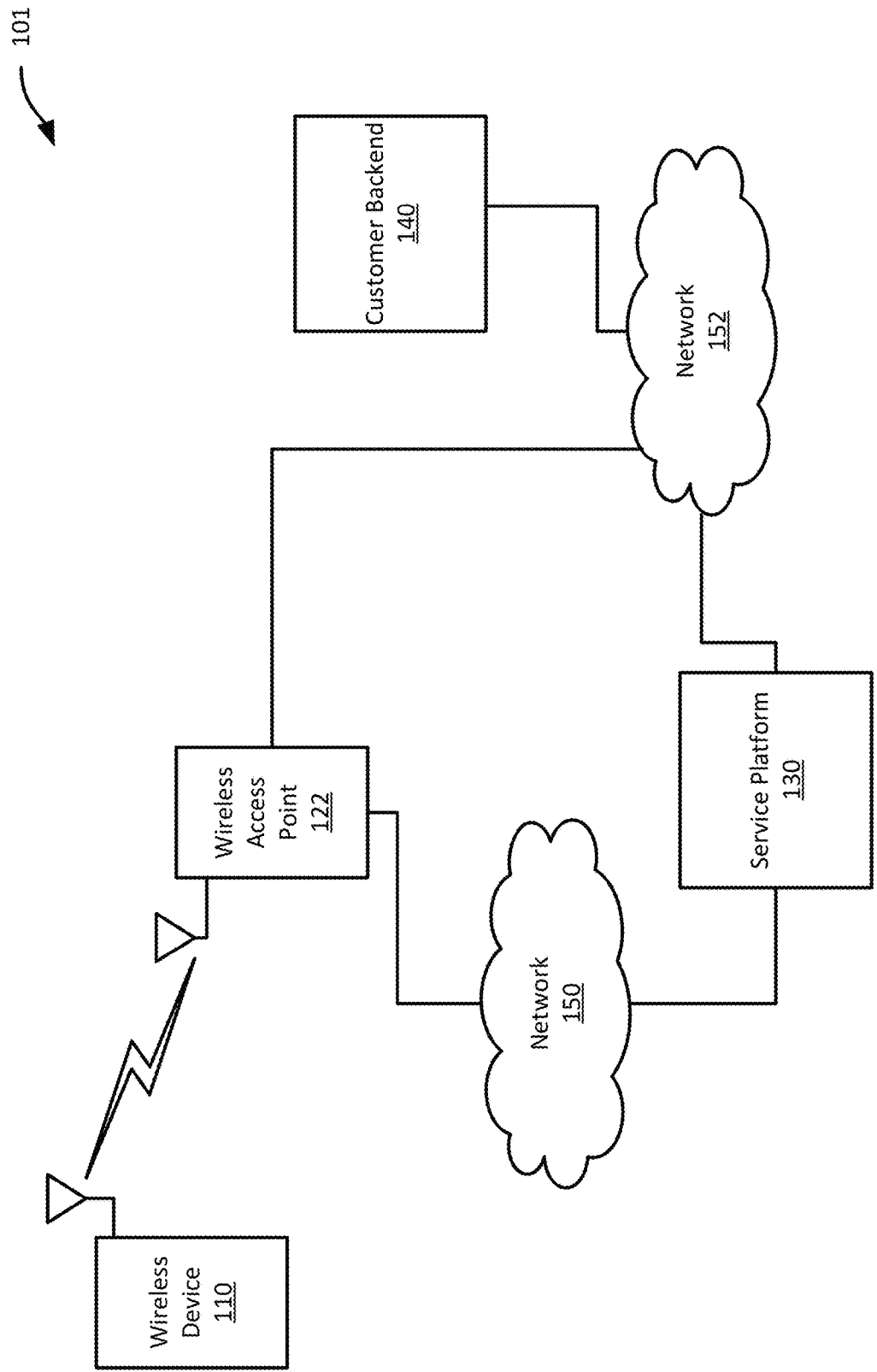

Referring now to FIG. 1B, FIG. 1B shows an example system 101 for dynamic provisioning of wireless devices with health gateways. The system 101 includes a wireless device 110 and a wireless access point 122 that are able to communicate wirelessly with each other, either directly over a wireless medium or indirectly via one or more intermediary devices as discussed above. The wireless AP 122 is connected via a network 150 to service platform 130, which is connected via network 152 to a customer backend 140.

The system 101 shown in FIG. 1B operates in generally the same manner as the system 100 shown in FIG. 1A; however, the wireless AP 122 operates as a pass-through device to connect the wireless device 110 directly to with the service platform 130. The wireless device 110 then exchanges messages with the service platform 130 to determine whether wireless device 110 should continue to communicate using the wireless AP 122. For example, the service platform 130 may provide information about its available services and, if those available services do not correspond with the data provided by the wireless device 110 or other configuration parameters stored on the wireless device 110, the wireless device 122 may disconnect from the wireless AP 122 and designate it is unsuitable. For example, the service platform 130 may provide services related to heart monitoring and diagnostics, while the wireless device 122 provides blood oxygen levels and respiration information. Thus, the services provided by the service platform 130 may be incompatible with the data provided by the wireless device 122.

It should be appreciated that the wireless AP may communicate with the wireless device 122 via any suitable wireless protocol, including Bluetooth, BLE, WiFi, cellular protocols, ZigBee, any suitable 802.11, 802.15, or 802.16 techniques, etc., according to this disclosure. Further, the wireless AP may provide health gateway functionality, by may also provide other services, such as those that may be provided by Internet-of-Things ("IOT") hubs (e.g., streaming movies or TV shows, online shopping, internet search features, etc.) or other general purpose computers.

Figure 2:
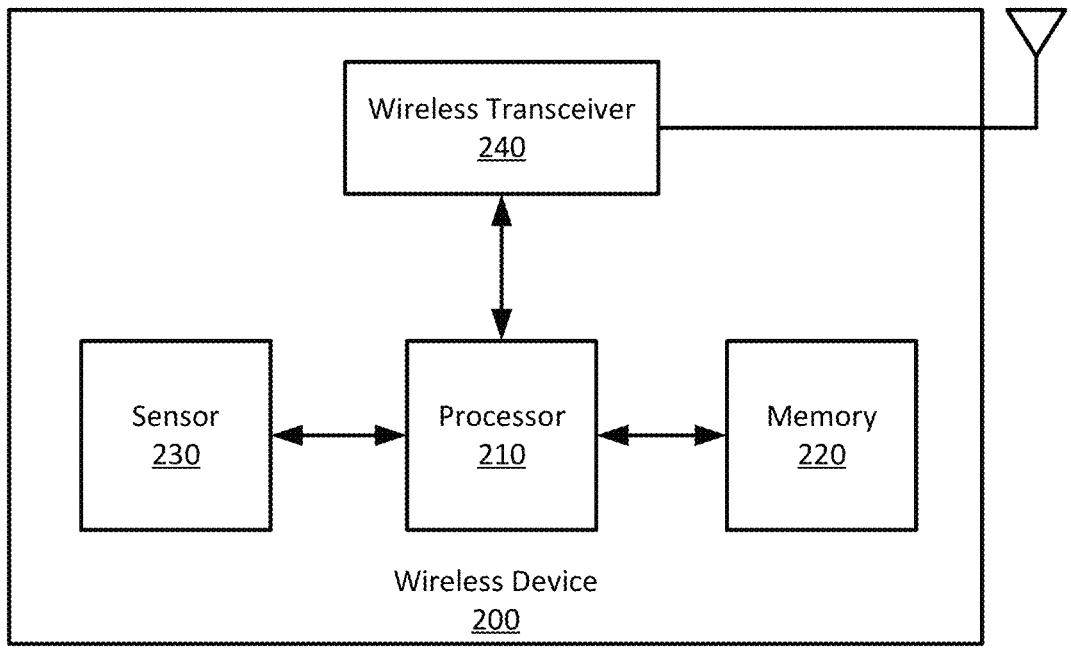
FIG. 2 shows an example wireless device for dynamic provisioning of wireless devices with health gateways.

Referring now to FIG. 2, FIG. 2 shows an example wireless device 200 suitable for dynamic provisioning with health gateways. The wireless device 200 includes a processor 210, which is in communication with a memory device 220, one or more sensors 230, and a wireless transceiver 240. In some examples, the wireless device 200 is battery powered, though in other examples, the wireless device 200 may be powered by inductive coupling with a power source or via a near-field communication ("NFC") device.

One or more sensors 230 may be bodily incorporated into the wireless device 200 or may be external to the wireless device 200 and may communicate with the wireless device 200 via a wired or wireless connection, including any suitable NFC technique. For example, a pulse sensor may worn on the patient's body, e.g., the patient's ear, and may communicate wirelessly with a smartwatch worn on the patient's wrist, which may include an ECG sensor or an oxygen saturation sensor.

The wireless transceiver 240 may use any suitable wireless communications technique, such as BLE, conventional Bluetooth, WiFi, WiFi direct, ZigBee, any suitable 802.11, 802.15, or 802.16 techniques, NFC, etc. Based on the wireless communications technique employed by the wireless transceiver 240, the wireless device 200 may broadcast packets to announce its presence to nearby wireless devices, such as a health gateway, or the wireless device 200 may listen for broadcast packets transmitted by a health gateway. Using such techniques, the wireless device 200 may begin a dynamic provisioning process with a health gateway.

Figure 3:
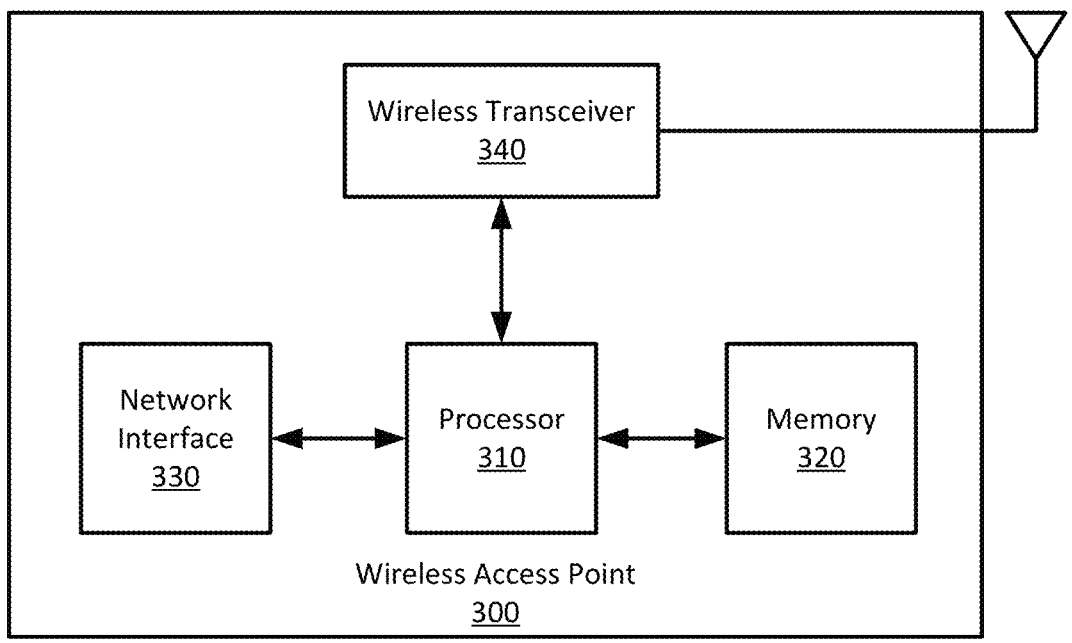
FIG. 3 shows an example wireless access point for dynamic provisioning of wireless devices with health gateways.

Referring now to FIG. 3, FIG. 3 shows an example wireless AP 300 providing health gateway functionality suitable for dynamic provisioning with health gateways. The wireless access point 300 includes a processor 310, which is in communication with a memory device 320, a network interface 330, and a wireless transceiver 340.

As with the wireless device 200, the wireless transceiver 340 may use any suitable wireless communications technique, such as BLE, conventional Bluetooth, WiFi, WiFi direct, ZigBee, IEEE 802.15.4-compliant techniques, NFC, etc. Based on the wireless communications technique employed by the wireless transceiver 340, the wireless AP 300 may broadcast packets to announce its presence to nearby wireless devices, such as wireless devices 110 or 200, or the health gateway 300 may listen for broadcast packets transmitted by a wireless device. Using such techniques, the health gateway 300 may begin a dynamic provisioning process with a wireless device.

The network interface 330 provides a communications interface to a network, such as the networks 150, 152 shown in FIG. 1A. Suitable network interfaces 300 include Ethernet, WiFi, cellular, or any other wired or wireless networking interface. Further, suitable authentication protocols may include the Access Network Query ("ANQ") Protocol, such as using a WiFi communications link.

The processor 330 may execute program code stored in memory 320 to provide health gateway features, or may interact with another processor, e.g., via a dongle, co-processor, or other processing device, to provide health gateway features. Further, in some examples, the processor 310 may be a special-purpose processor such as a DSP (digital signal processor), GPU (graphics processing unit), or ASIC (application-specific integrated circuit) to provide signal modulation/demodulation functionality to enable wireless or other network connectivity. Such a special purpose processor may also provide the health gateway features, or communicate with another processor to provide such features.

Figure 4A:
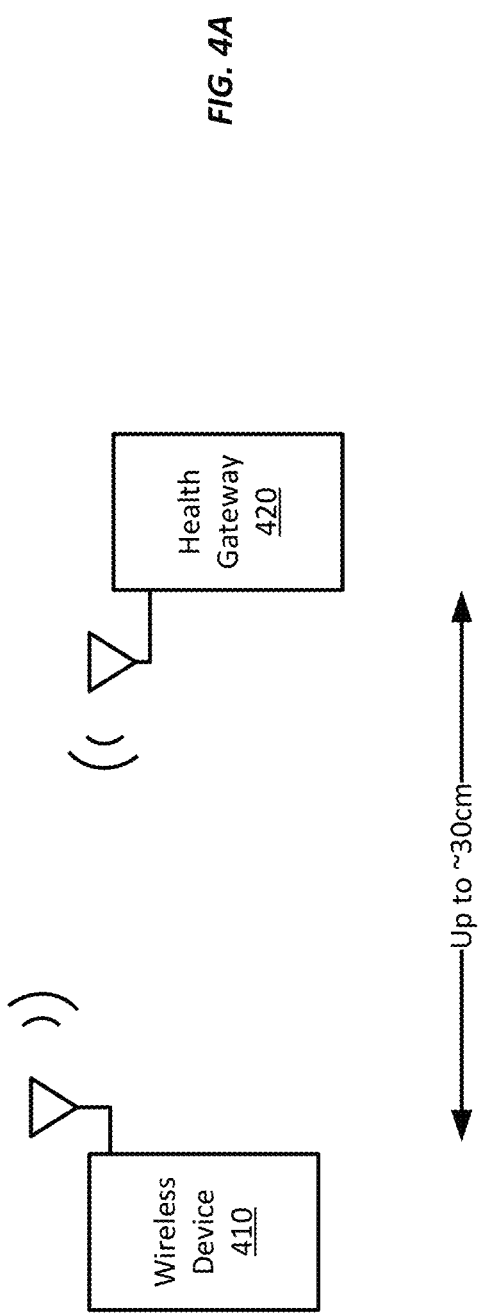
FIGS. 4A-4B and 5A-5B show example discovery techniques for dynamic provisioning of wireless devices with health gateways.
Figure 4B:
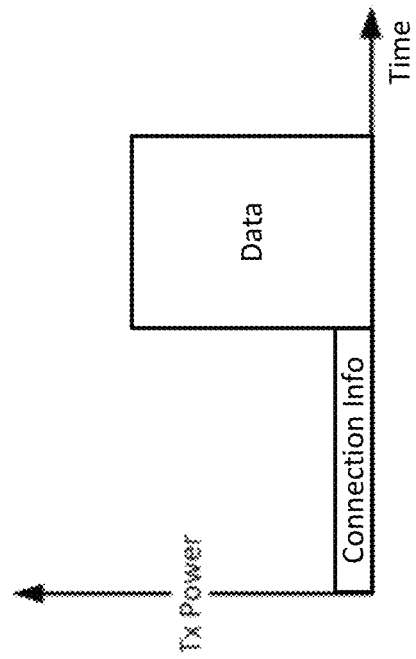

Referring now to FIGS. 4A-4B, FIGS. 4A-4B show an example discovery technique for dynamic provisioning of wireless devices with health gateways. In this example, a wireless device 410 and a health gateway 420 are attempting to discover nearby wireless devices. Wireless device 410 is any suitable wireless device according to this disclosure, such as wireless device 110 or 200, while health gateway 420 is any suitable health gateway according to this disclosure, such as health gateway 120 or 300.

According to different examples, one of the devices 410, 420 transmits wireless broadcast packets according to a wireless communications technique. In this example, the wireless device 410 transmits BLE advertising packets, while the health gateway 420 listens for such BLE advertising packets. One format for an example BLE advertising packet is shown in FIGS. 6A-6B and 7A-7B, discussed in more detail below.

The wireless device 410 transmits advertising packets at a low transmit power to help ensure that it is only discovered by wireless devices within a short range, in this case within 30 centimeters ("cm"). Such a technique may reduce the chances of the wireless device 410 attempting to provision with the wrong health gateway or other wireless device or AP, such as in a public environment or a more densely-populated electronic environment at a hospital, doctor's office, clinic, etc. Thus, a reduced transmit power may indicate to the wireless device 410 that if a health gateway receives and responds to an advertising packet, the health gateway is within close physical proximity to the wireless device 410. Similarly, a health gateway 420 communicating with such a wireless device 410 may infer that it is communicating with a device in close proximity. At a later time, after the wireless device 410 has provisioned with the health gateway 420, it may transmit data at a stronger transmit power to enable longer-distance communications, e.g., 30 meters or more. FIG. 4B illustrates the difference in transmit power between the advertising packet—labelled "connection info"—and data that is later transmitted after provisioning is complete.

Such a technique may provide a relatively secure, close-proximity means for discovering a nearby health gateway. Alternatively, the health gateway 420 may transmit broadcast packets at a low transmit power and a wireless device 410 brought within close proximity to the health gateway, e.g., within 30 cm, may then respond, and the health gateway 420 may determine that the wireless device 410 is one that may be provisioned for use with the health gateway 420.

Figure 5A:
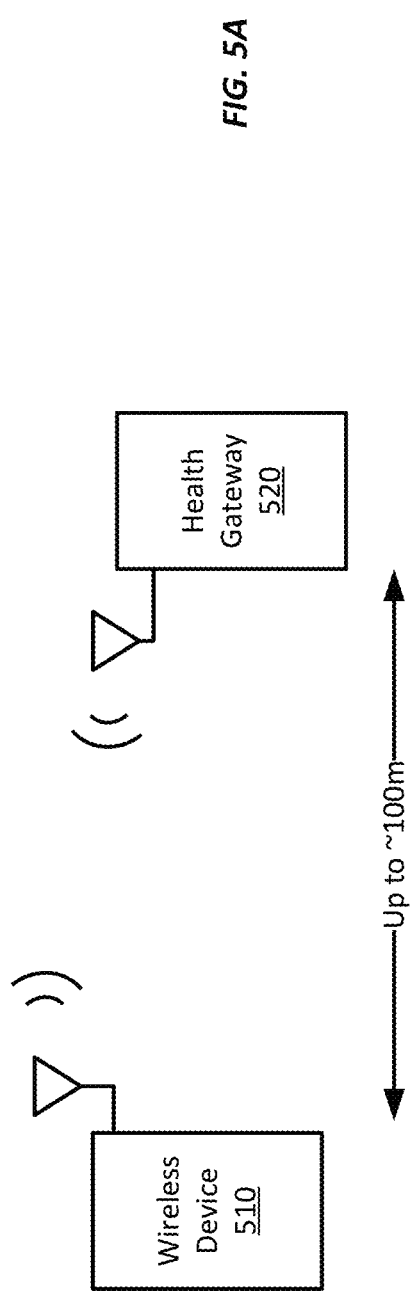
Figure 5B:
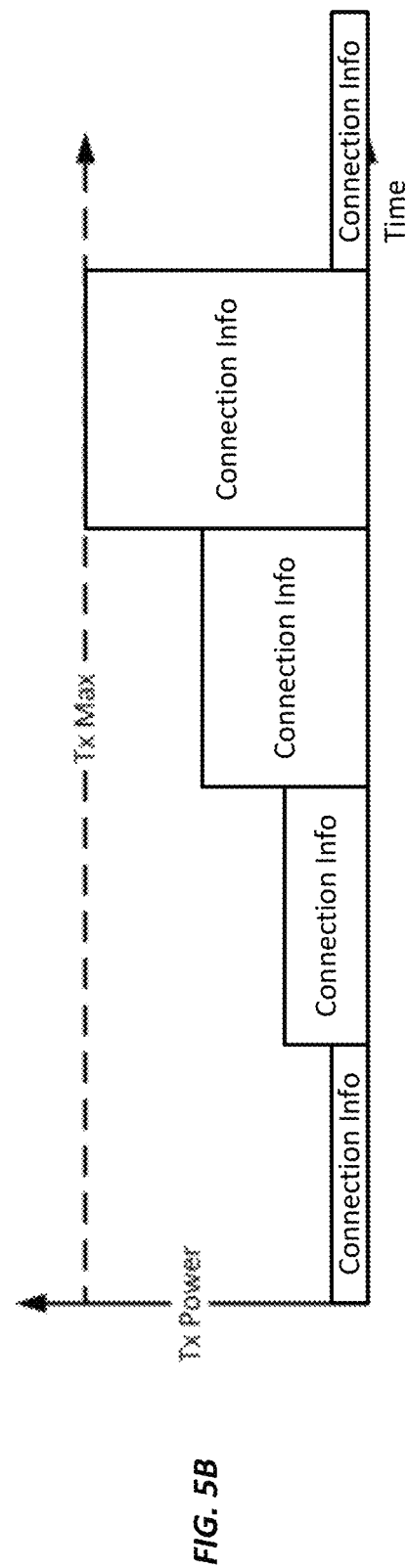

Referring now to FIGS. 5A-5B, FIGS. 5A-5B show another example discovery technique for dynamic provisioning of wireless devices with health gateways. In this example, a wireless device 510 and a health gateway 520 are attempting to discover nearby wireless devices.

As discussed above with respect to FIGS. 4A-4B, according to various examples, one of the devices 510, 520 transmits wireless broadcast packets according to a wireless communications technique. In this example, the wireless device 510 transmits BLE advertising packets, while the health gateway 520 listens for such BLE advertising packets.

The wireless device 510 initially transmits advertising packets at a low transmit power to ensure that it is only discovered by a health gateway within a short range, in this case within 30 centimeters ("cm"); however, in this example, if no response is received from a health gateway 520, the wireless device 510 progressively increases the transmit power until either a health gateway 520 responds, or a maximum transmit power is reached, which may provide a transmission range of up to 100 meters or more.

Such a technique may increase the chances of the wireless device 510 locating and provisioning with a health gateway.

For example, if the patient is at home and thus any discovered health gateways are highly likely to be the patient's own health gateway, such a technique may enable a wireless device 510 to more quickly discover the health gateway 520 by progressively broadcasting advertising packets with greater transmit power, hence providing a greater transmission range. Alternatively, the health gateway 520 may transmit broadcast packets according to such a scheme and a wireless device 510 within range of any of the broadcasted packets, may then respond at an appropriate power level, and the health gateway 520 may then determine whether the wireless device 510 is one that may be provisioned for use with the health gateway 520.

While the examples discussed with respect to FIGS. 4A-5B employed the BLE communications technique, any other suitable wireless communications technique may be employed. Such techniques have their own particular broadcasting and discovery protocols, but may be employed with the example transmit power schemes discussed with respect to FIGS. 4A-5B.

Figure 6A:
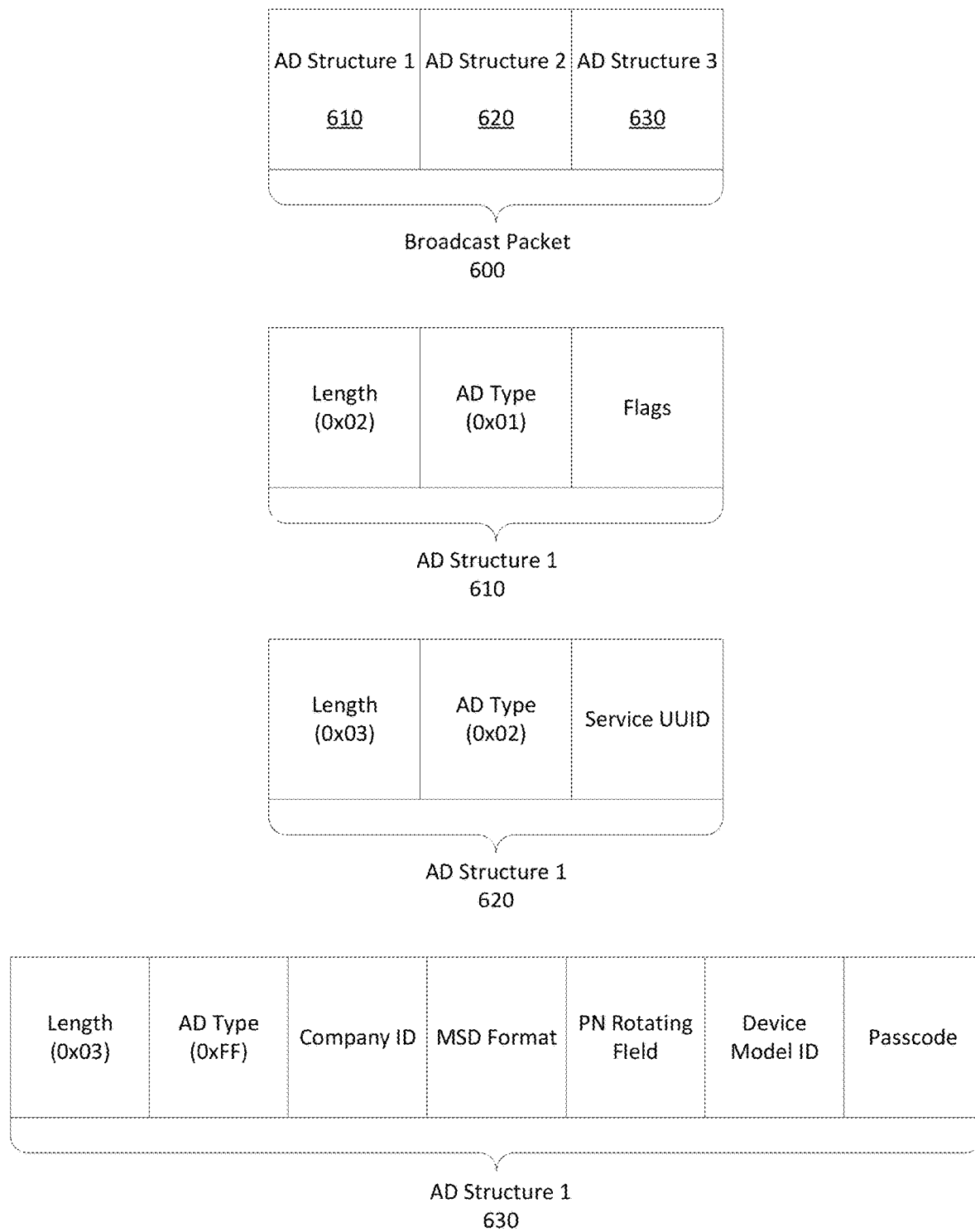

Referring now to FIGS. 6A-6B, FIGS. 6A-6B shows an example packet format 600 for a broadcast packet according to one example. In this example, the broadcast packet 600 is formatted for a BLE-based example. Such a packet format may be used to send BLE advertising packets in some examples. As can be seen, the broadcast packet 600 includes fields specific to the BLE protocol, as well as fields suitable for carrying information to identify the device, the manufacturer and other information usable to identify the broadcasting device to the receiving device for identification and provisioning. For example, the first packet segment format 610 shown in FIGS. 6A-6B includes fields indicating the length of the packet, the advertisement type (e.g., flags), and flag values. The second packet segment format 620 includes fields indicating the length of the packet, the advertisement type, and a UUID value. Further, the third packet segment format 630 also includes length and advertisement type fields, but also includes other information, including manufacturer specific data ("MSD"), a company ID code, and a model ID of the broadcasting device, which may indicate, for example, a medical device type or a health gateway identifier.

Further, in some examples, the third packet segment format 630 may include an optional passcode field. In this example, the MSD information specifies whether the passcode field is present. Further, the MSD information may specify whether the packet is an advertisement packet that a health gateway may use to try to pair with the transmitting device, or whether the packet is a post-discovery-phase packet used to communicate between the transmitting device and the health gateway. An example of a packet format without a passcode field is described with respect to FIGS. 7A-7B.

Manufacturer-specific data may indicate the type of device, the version (or model) of the device, expiration information about the device, lot or unit information, etc. The company ID code may be a numeric value associated with (or assigned to) a particular company. For example, company A may manufacture inhalers and may have an ID of 0x45AB. The company ID code—0x45AB—may be included in addition to information about the particular device, and may be used to determine packet formats, data type, or other processing appropriate for received data packets. A model ID may indicate the type of wireless device, or a particular model of wireless device. For example, the model ID may indicate that the wireless device is an inhaler, an EKG sensor, a smartwatch, etc. It may also indicate (or instead indicate) the particular type of device, such as an inhaler with 15 doses or an inhaler with 30 doses, etc. The MSD version number may indicate a particular version of the transmitting device, e.g., version 1.1A, etc.

Still other packet formats may be employed with different fields or different numbers of fields according to different examples.

A wireless device receiving such a packet may analyze the information carried in the payload of the packet to determine whether the broadcasting device is suitable for provisioning. For example, a company ID along with a model ID may indicate the type of device broadcasting the packet, e.g., a health gateway or a patient device (e.g., an inhaler). The device receiving the broadcast packet may employ such information, such as by identifying the payload information as corresponding to a known type and model of device.

Figure 7A:
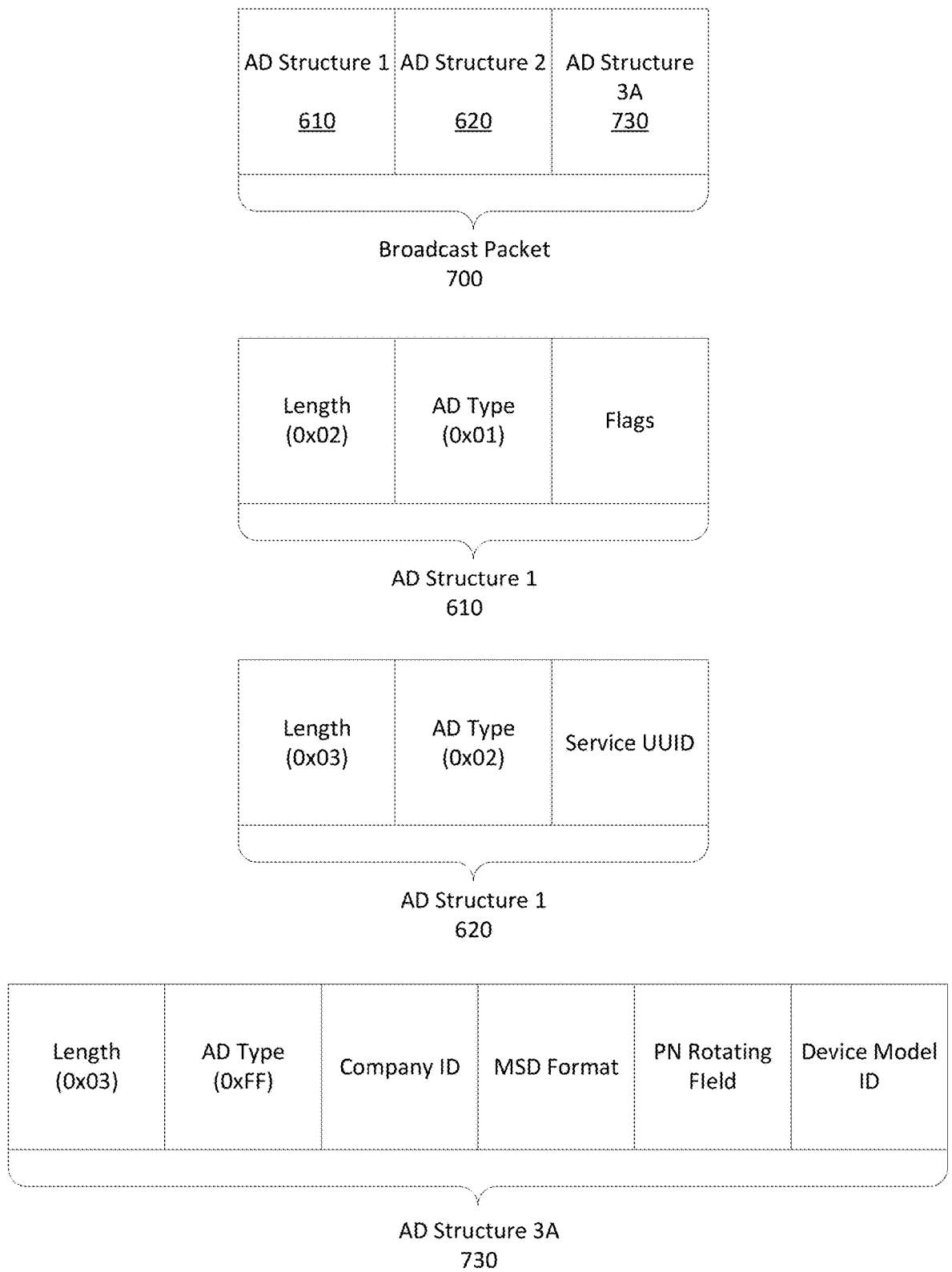

Referring now to FIGS. 7A-B, FIGS. 7A-B shows another example packet format 700. The example packet format 700 shown in FIGS. 7A-7B may be employed similarly as the packet format 600 discussed above with respect to FIGS. 6A-6B. In some examples, however, the packet format 700 may be employed for post-discovery data transmissions. For example, after a wireless device is recognized and provisioned by a health gateway, the wireless device may communicate using the packet format 700 shown in FIG. 7A, which includes AD data of arbitrary length. Further, AD structure 3A 730 used in this example packet format lacks the passcode field of AD structure 3 630 shown in FIGS. 6A-6B. A wireless device may then specify the service UUID corresponding to the data carried in the packet to allow the health gateway to properly route the data according to the corresponding service, e.g., blood pressure monitoring, inhaler usage monitoring, maintenance medication usage monitoring, etc. Such a packet format may enable more efficient communications between a provisioned wireless device and a service platform or other health care backend.

In this example, the value of the MSD information may specify the broadcast packet format. For example, the MSD information may include a bit-field value with the following corresponding packet format:

| MSD Bit Field | MSD Description | Broadcast Packet Format |
|---|---|---|
| 0x00 | Passcode is not present; discovery advertisement (new health gateway can try to pair/connect) | Broadcast Packet 700 |
| 0x01 | Passcode is present; discovery advertisement (new health gateway can try to pair/connect) | Broadcast Packet 600 |
| 0x02 | Passcode is not present; discovery advertisement for specific health gateway(s) to provide dedicated connection windows | Broadcast Packet 700 |
| 0x03 | Passcode is not present; non-discovery advertisement (new hub not to try to pair/connect); may be used in post discovery phase for communication with paired health gateway(s) | Broadcast Packet 700 |

Figure 8:
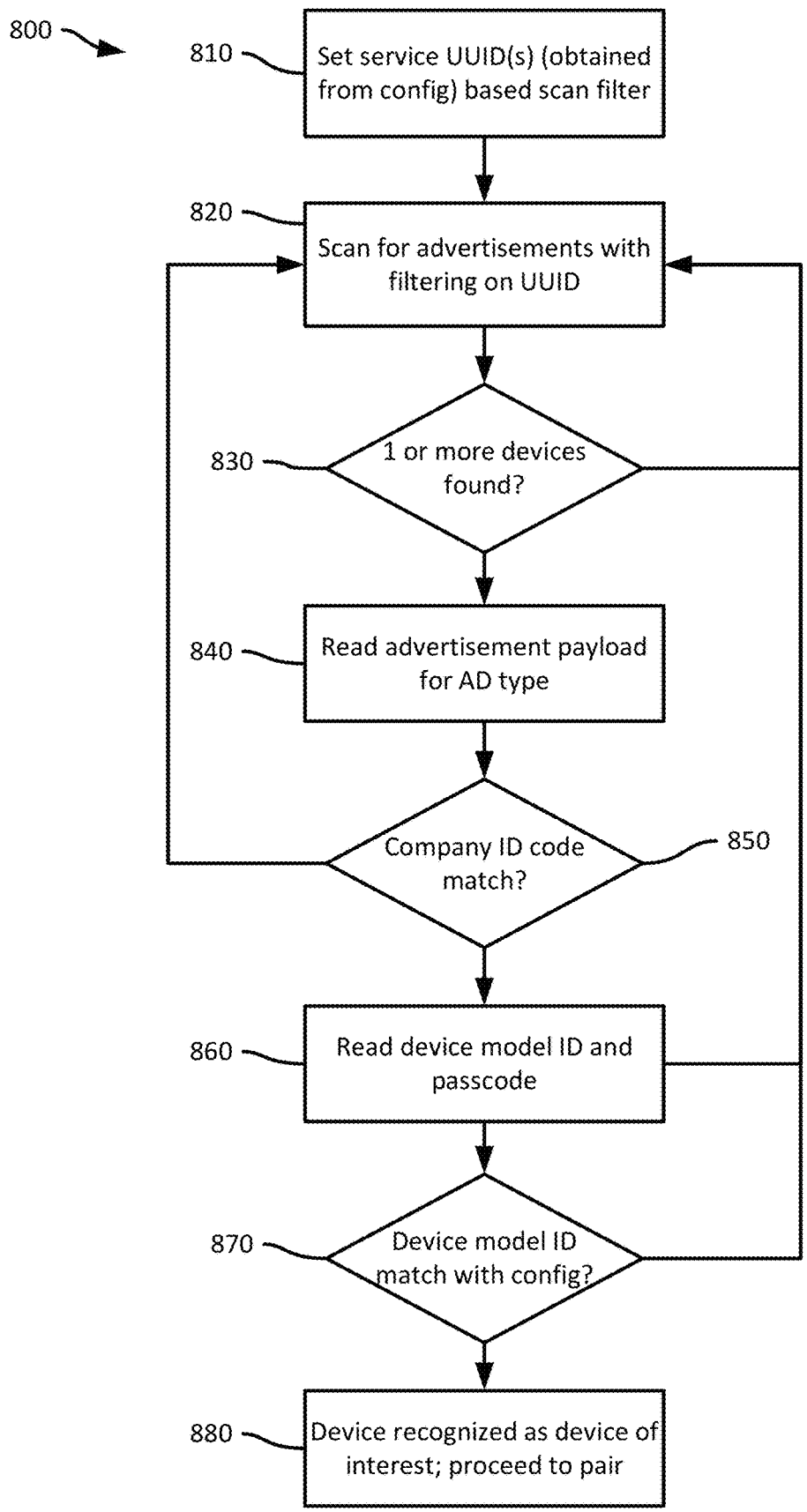
FIGS. 8-13 show example methods for dynamic provisioning of wireless devices with health gateways.

Referring now to FIG. 8, FIG. 8 shows an example method 800 for dynamic provisioning of wireless devices with health gateways. The method 800 will be described with respect to the system 100 shown in FIG. 1A; however, any suitable system according to this disclosure may be employed. Further, the method 800 will be described as being performed by the health gateway 120; however, in other examples, it may be performed by the wireless device 110. Further, this example is described with respect to an example health gateway 120 employing a BLE communications technique; however, any other suitable communications technique may be employed. For example, in one example, the health gateway employs WiFi and the ANQ protocol.

At block 810, the health gateway 120 establishes a scan filter based on one or more Service UUIDs. Service UUIDs may be associated with a service provider 130 or a client backend 140 in some examples. In this example, the health gateway 120 has been provided a configuration file from the service provider 130 with one or more Service UUIDs. Such a configuration file may be in a comma-delimited format, an HTML or XML file, or according to any other suitable file format. A service UUID may indicate a type of service provider, such as the identity of a health care provider, insurer, customer backend provider (e.g., a cloud service provider ID), etc. In some examples, service information, such as the service UUID, may identify a specific type of service, such as asynchronous events (e.g., inhaler usage, epinephrine injection, etc.), planned events (e.g., medication dosage according to a prescription, such as once every 6 hours), continuous monitoring (e.g., heartrate, blood pressure, etc.), fixed-duration monitoring (e.g., post-surgery monitoring for three weeks), etc. The service UUID may be used to both identify whether a wireless device is appropriate for provisioning, but may also be employed to provision the device with the correct service platform or customer backend. A service UUID may be a value provided by a particular service platform that is substantially unique on its own, or it may be combined with other data, such as a device type, manufacturer ID, etc. to uniquely identify a service platform.

At block 820, the health gateway 120 activates its receiver to discover any wireless devices transmitting broadcast packets. In some examples, a health gateway may maintain its receiver as active to receive broadcast requests at any time, though in some examples, the health gateway may only activate its receiver periodically, e.g., every 5 seconds for a period of 2 seconds. A continuously active receiver may be advantageous because it allows reception of a broadcast packet at any time, which may allow faster provisioning of a device; however, it may consume more power, and thus may be more suitable to devices connected to an external power supply. In contrast, a battery-powered health gateway may conserve power by only activating its receiver periodically. Though it should be appreciated that any suitable health gateway may use any suitable activation scheme for its wireless receiver.

After receiving a broadcast packet, such as a packet constructed according to the formats described with respect to FIG. 6 or 7 above, the health gateway determines whether a service UUID in the packet meets the established filters. If the packet has a matching or recognized service UUID, the method proceeds to block 830; however, if the packet does not have a matching or recognized service UUID, the packet is discarded and a new packet is awaited. To determine whether the service UUID satisfies the established filter(s), the service UUID in a packet may be matched to an approved listing of service UUIDs, such as service UUIDs supported by the health gateway, or services that are blocked by the health gateway. In some examples, the health gateway may only determine whether the service UUID is a recognized UUID, irrespective of any other information, such as whether the UUID is approved or supported. Further, the health gateway may receive information about supported services from a customer backend or service provider.

At block 830, if no devices are discovered, the method 800 returns to block 820 to continue to attempt to discover wireless devices. Otherwise, the method 800 proceeds to block 840.

At block 840, the health gateway 120 extracts information from the payload of each broadcast packet received, including a company ID code and a model ID in this example. For example, the health gateway may extract information from the packet described with respect to FIGS. 6-7 above.

At block 850, for each received broadcast packet, the health gateway 120 determines whether the company ID code matches a known company ID code. If so, the method 800 proceeds to block 860. Otherwise, it discards the broadcast packet and processes the next received broadcast packet, if any. If no others remain to be processed, the method 800 returns to block 820.

At block 860, the health gateway 120 extracts a device model ID and a BLE passcode from each remaining broadcast packet. In some examples, the health gateway may determine that the wireless device is attempting to connect based on the presence of the passcode, and if no passcode is provided, may discard the packet and return to block 820. If the BLE passcode is present and correct, the method proceeds to block 870, otherwise, the packet is discarded and the method 800 returns to block 820.

At block 870, if the model ID matches a known or authorized model ID, the method 800 proceeds to block 880. Otherwise, the method 800 returns to block 820.

At block 880, the health gateway 120 determines that the device that transmitted the broadcast packet is suitable for provisioning, based on successfully completing one or more of the prior portions of the method 800, and registers the device and pairs with it to establish wireless communications.

After the method 800 completes block 880, the health gateway 120 may return to block 810 or 820 to locate and provision additional wireless devices.

Figure 9:
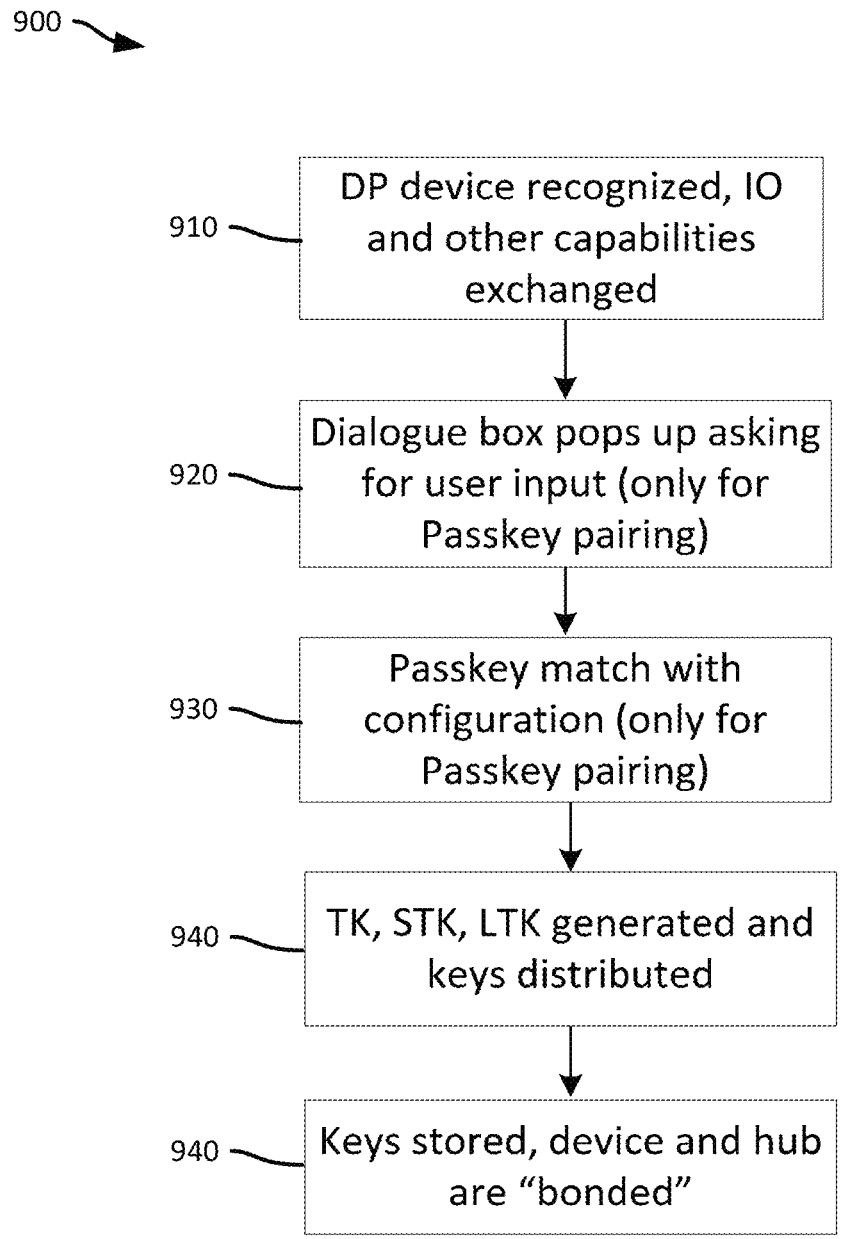

Referring now to FIG. 9, FIG. 9 shows an example method 900 for dynamic provisioning of wireless devices with health gateways. The method 900 will be described with respect to the system 100 shown in FIG. 1A; however, any suitable system according to this disclosure may be employed. Further, the method 900 will be described as being performed by the health gateway 120; however, in other examples, it may be performed by the wireless device 110. Further, this example is described with respect to an example health gateway 120 employing a BLE communications technique; however, any other suitable communications technique may be employed.

At block 910, the health gateway recognizes a dynamic pairing wireless device 110, such as discussed above with respect to FIG. 8. In this example, the health gateway and the wireless device 110 exchange packets that describe capabilities, such as sensor types, data formats, etc.

At block 920, the health gateway displays a dialog box on its display screen requesting patient input for a passcode.

At block 930, if the passcode matches, the method 900 proceeds to block 940, otherwise the pairing fails.

At block 940, a BLE temporary key ("TK"), short-term key ("STK"), and long-term key ("LTK") are generated and distributed by the health gateway 120 to the wireless device 110.

At block 950, the health gateway 120 creates a record for the wireless device 110 and associates the TK, STK, and LTK with the record to enable current and future communications with the wireless device 110, thereby provisioning the wireless device 110.

After the health gateway 120 completes the processing at block 950, it may restart the method 900 to provision additional wireless devices.

Figure 10:
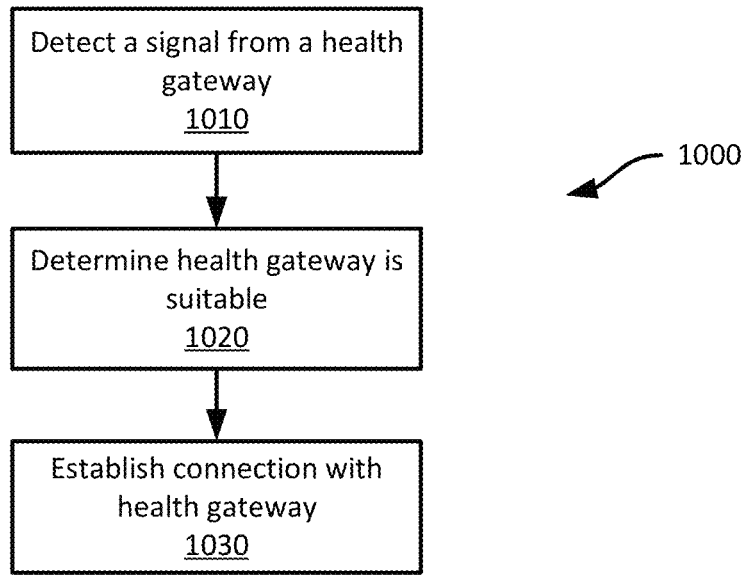

Referring now to FIG. 10, FIG. 10 shows an example method 1000 for dynamic provisioning of wireless devices with health gateways. The method 1000 will be described with respect to the system 100 shown in FIG. 1A; however, any suitable system according to this disclosure may be employed. Further, this example is described with respect to an example wireless device 110 employing a BLE communications technique; however, any other suitable communications technique may be employed.

At block 1010, the wireless device 110 detects a signal from a health gateway 120. In this example, the wireless device 110 detects a broadcasted advertising packet transmitted by the health gateway 120. The advertising packet in this example includes information identifying the health gateway 120, the service provider 130, and the customer backend 140. In addition, the advertising packet also includes a passcode for the health gateway 120.

In some examples, rather than looking for broadcasted advertising packets, the wireless device 110 may transmit a point-to-point signal to a health gateway 120, and may receive a signal from the health gateway 120 in response, such as also described with respect to FIG. 12 below. For example, the wireless device 110 may be preprogrammed with RF parameters for the health gateway 120, such as frequency information, wireless protocol, security information, identity information for the health gateway 120, etc. A point-to-point transmission may provide added security benefits as it is directed to a specific device rather than to any device in proximity to the wireless device 110.

At block 1020, the wireless device 110 determines whether the health gateway 120 is suitable for wireless communications, such as described above with respect to FIG. 8. In this example, however, the wireless device 110 extracts information from the broadcast packet and compares it with configuration information stored on a memory of the wireless device 110. For example, the wireless device 110 may check a list of known health gateways (or health gateway manufacturers, service providers, customer backends, etc.) to determine whether the identified health gateway 110 is known. If it is known, the wireless device 110 determines whether it is suitable or not, such as based on a record stored in a memory of the wireless device 110. If the health gateway 120 is not recognized, the wireless device 110 determines whether identification information for the service provider 130 or the customer backend 140 matches service provider information or customer backend information, e.g., for the patient, stored in memory on the wireless device 110. If a match is detected for either or both, the wireless device 110 determines that the health gateway is suitable. Otherwise, the wireless device 110 determines that the health gateway 120 is not suitable, discards the broadcast packet, and stores a record with identification information for the health gateway 120 indicating it as not being suitable.

In some examples, to determine whether the health gateway 120 is suitable, the wireless device 110 determines whether a service platform 130 in communication with the health gateway 120 is compatible with information available to, or sensed by, the wireless device. For example, the health gateway 120 may provide a communications link to a cardiology service platform, while the wireless device 110 provides health data related to other physiological events, such as blood oxygen, blood glucose, etc. Thus, while the wireless device 110 and the health gateway 120 are compatible, the wireless device 110 may determine the health gateway 120 is not suitable for wireless communications due to a mismatch between the wireless device 110 and the service platform 130 (or the customer backend 140, e.g., due to it relating to the wrong hospital or insurance provider). Alternatively, if the service platform 130 or customer backend 140 are compatible with the wireless device 110, or the identified patient, etc., the wireless device 110 may determine that the health gateway 120 is suitable.

Further, in some examples, the wireless device 110 may determine whether the physical link between the wireless device 110 and the health gateway 120 is suitable to propagate data from the wireless device 110 to the service platform 130 or customer backend 140. For example, a wireless protocol employed by the health gateway 120 may be incompatible with data to be transmitted by the wireless device 110, e.g., a payload size is too large or a required data rate is too high, or may require signaling not supported by the health gateway 120. Thus, the wireless device 110 may determine that a health gateway 120 is unsuitable based on characteristics of an available physical connection to the health gateway 120.

At block 1030, the wireless device 110 attempts to establish a connection with the health gateway 120. For example, the wireless device 110 may establish a connection using the passcode received from the health gateway. In some examples, the wireless device 110 may instead transmit information about the wireless device 110 to the health gateway, such as the information described above with respect to the packet shown in FIGS. 6A-6B and 7A-7B or as discussed above with respect to the method 800 of FIG. 8. The health gateway 120 may then determine whether the wireless device 110 is one authorized to be connected to the health gateway 120. If so, a wireless connection is established. Such an example may be part of a two-way provisioning process, and may incorporate portions or, or the entireties of, other example methods according to this disclosure, such as the methods described with respect to FIG. 10, 11, or 13. The method 1000 may then terminate, or an example method, such as the method 1000 of FIG. 10, may be performed to provision the wireless device 110 with another health gateway.

Figure 11:
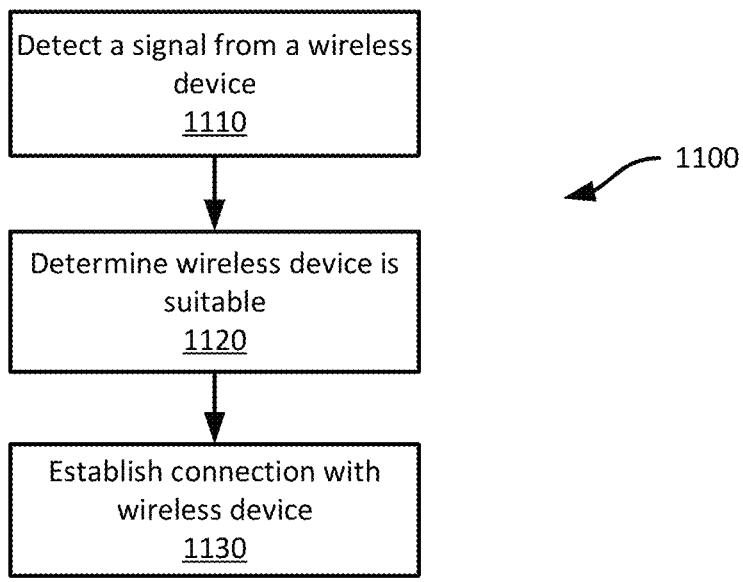

Referring now to FIG. 11, FIG. 11 shows an example method 1100 for dynamic provisioning of wireless devices with health gateways. The method 1100 will be described with respect to the system 100 shown in FIG. 1A; however, any suitable system according to this disclosure may be employed. Further, this example is described with respect to an example health gateway 120 employing a BLE communications technique; however, any other suitable communications technique may be employed.

At block 1110, the health gateway 120 detects a signal from a wireless device 110. In this example, the health gateway 120 detects a broadcast packet, e.g., an advertisement packet, transmitted by the wireless device 110. The broadcast packet in this example includes information identifying the wireless device 110, such as the information described above with respect to the packet formats shown in FIGS. 6A-6B and 7A-7B. In addition, the broadcast packet also includes a passcode for the wireless device 110.

In some examples, rather than detecting a broadcast signal, the health gateway 120 may detect a point-to-point transmissions from the wireless device 110. For example, the wireless device 110 may be preprogrammed with RF parameters for the health gateway 120, such as frequency information, wireless protocol, security information, identity information for the health gateway, etc. Thus, the health gateway 120 may detect such a point-to-point transmission and process the received data. Alternatively, the wireless device 110 may transmit a signal to the health gateway 120 in response to receiving a broadcast (or other) signal from the health gateway 120, such as described below with respect to FIG. 13. Further, in some examples, the health gateway may indirectly receive a signal transmitted by a wireless device 110. For example, the health gateway may communicate with the wireless device 110 via an intervening network component, such as a WiFi AP.

At block 1120, the health gateway 120 determines whether the wireless device 110 is suitable for connecting and provisioning. For example, the health gateway 120 may perform the method 800 described above with respect to FIG. 8. More generally, the health gateway 120 may determine whether the information provided by the wireless device 110 in the broadcast packet matches configuration information for suitable wireless devices stored at the health gateway 120 or based on a list of known unsuitable wireless devices.

In this example, the health gateway 120 receives device information from the wireless device 110, including a company ID code, manufacturer-specific data (e.g., a device type, a device name, etc.), and service information (e.g., cardiovascular monitoring, diabetes monitoring, respiratory monitoring, etc.), and may be compared against one or more databases identifying authorized companies, manufacturer-specific data, or available services. The database information may be received from a customer backend 140 or service provider 130 according to some examples, or may be preconfigured. Further, and while both device and service information are used in this example, in other examples, only one or the other may be required. If the health gateway 120 determines that the wireless device 110 is suitable for connecting and provisioning, the method 1100 proceeds to block 1130. Otherwise, the method 1100 terminates and the health gateway 120 generates a record stored in its memory with information identifying the wireless device 110 and indicating it is not suitable for communication.

At block 1130, the health gateway 120 establishes a connection with the wireless device 110 using the passcode and provisions it by creating a new record at the health gateway 120, and indicating the device as authorized or provisioned.

After completing the method 1100, the health gateway 120 may attempt to locate other wireless devices and restart the method 1100.

Figure 12:
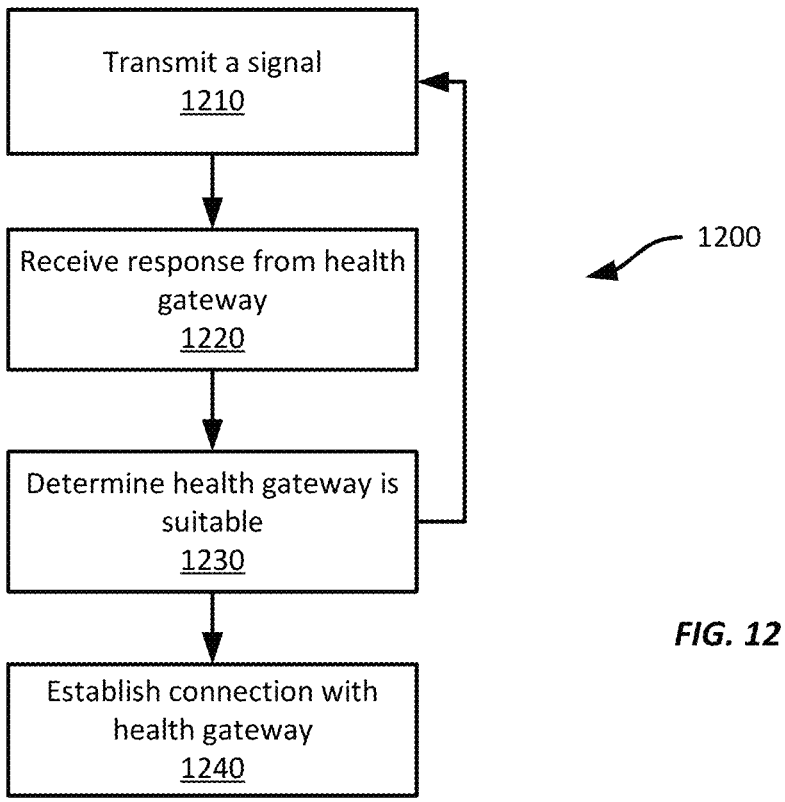

Referring now to FIG. 12, FIG. 12 shows an example method 1200 for dynamic provisioning of wireless devices with health gateways. The method 1200 will be described with respect to the system 100 shown in FIG. 1A; however, any suitable system according to this disclosure may be employed. Further, this example is described with respect to an example health gateway 120 employing a BLE communications technique; however, any other suitable communications technique may be employed.

At block 1210, a wireless device 110 transmits a signal to identify a health gateway 120 (or wireless AP 122) to connect to. In this example, the wireless device 110 transmits a broadcast signal including a packet according to the packet formats shown in FIGS. 6A-6B and 7A-7B, which indicates the service UUID, the manufacturer-specific data, and the device model ID. In some examples, the signal may be a request to connect or a request for information from the health gateway 120.

The wireless device 110 in some examples, may periodically transmit such a broadcast signal until a response is received from a health gateway 120, or it may only transmit the signal in response to an explicit request from a patient, such as in response to the patient pressing a button, shaking the device, or otherwise indicating the device is to connect with a health gateway 120. In some examples, the wireless device 110 may transmit the signal in response to detecting the presence of a health gateway 120, such as by detecting a beacon or other signal broadcast by the health gateway 120.

In some examples, the wireless device 110 may transmit the signal even if it is already connected to a wireless AP or health gateway. For example, the wireless device 110 may communicate with multiple wireless APs or health gateways in some examples, such as to provide different types of information to two or more different health gateways, or to communicate with health gateways that are connected to different service platforms or customer backends. In one example, different health gateways may be configured to connect with wireless devices having specific data within a broadcast (or other) packet. For example, the wireless device 110 may transmit a broadcast packet having one type of manufacturer-specific data, which is accepted by a first health gateway, but rejected by a second health gateway. The wireless device 110 may then transmit a broadcast packet having a second type of manufacturer-specific data, which is then accepted by the second health gateway, but rejected by the first health gateway. Such a technique may reduce contention when multiple wireless devices 110 are attempting to connect to available health gateways. And while the wireless device 110 used different manufacturer-specific data in this example, other portions of the broadcast packet may be varied according to different examples to connect to different health gateways.

At block 1220, the wireless device 110 receives a response from the health gateway 120 to the transmitted signal. In this example, the wireless device 110 receives a packet that indicates that the health gateway 120 supports the service UUID and the manufacturer-specific data. In some examples, the response packet may be an acknowledgement or an approval. In some examples, the health gateway 120 may transmit a packet indicating the supported service UUIDs and manufacturer-specific data, which may be used at block 1230 to determine if the health gateway 120 is suitable for use.

At block 1230, the wireless device 110 determines whether the health gateway 120 is suitable to communicate with, such as described above with respect to FIG. 8. For example, if the health gateway 120 responded to the wireless device 110 indicating the information provided by the wireless device 110 is compatible, the wireless device 110 may determine that the health gateway 120 is suitable to communicate with. If the health gateway 120 responds with supported service UUIDs or manufacturer-specific data, the wireless device 110 may determine whether the health gateway 120 is suitable for use based on the wireless device's configuration, such as configured service UUIDs or manufacturer-specific data stored in the wireless device 110. If the health gateway 120 is suitable, the method proceeds to block 1240, otherwise, the method 1200 returns to block 1210 and the wireless device 110 may transmit another signal.

At block 1240, the wireless device 110 establishes a communications connection with the health gateway 120. For example, the wireless device 110 may establish a BLE or WiFi connection with the health gateway 120 after determining it is suitable at block 1230.

While the method of FIG. 12 was described with respect to a wireless device 110 communicating with a health gateway 120, it should be appreciated that the method may be employed with respect to any suitable wireless AP or health gateway according to this disclosure.

Figure 13:
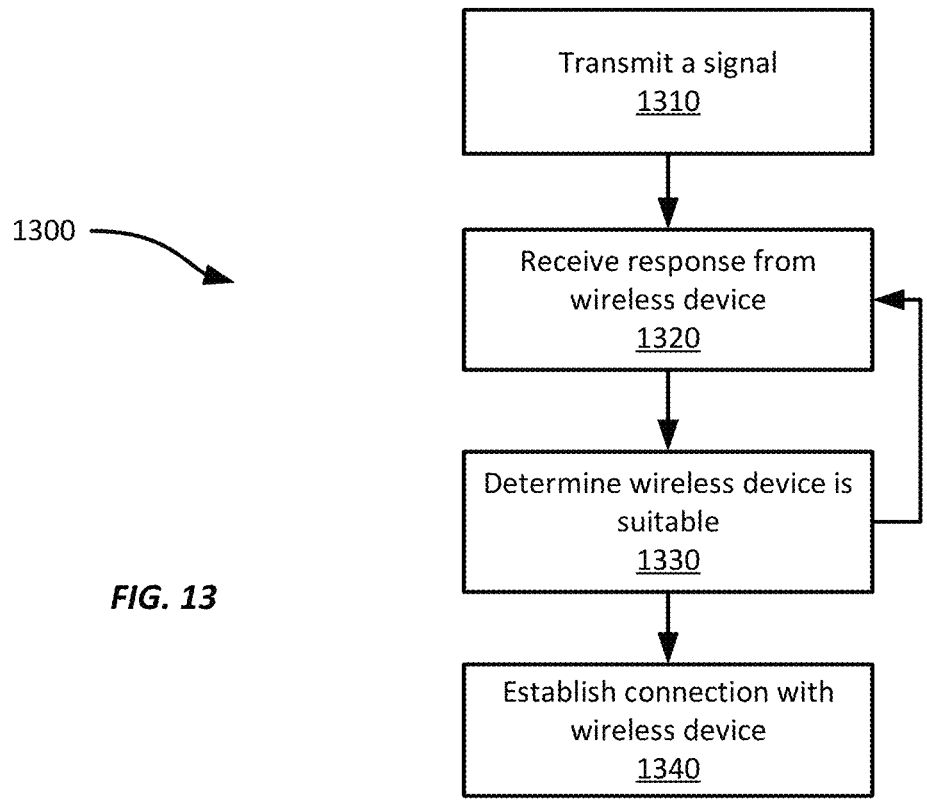

Referring now to FIG. 13, FIG. 13 shows an example method 1300 for dynamic provisioning of wireless devices with health gateways. The method 1300 will be described with respect to the system 100 shown in FIG. 1A; however, any suitable system according to this disclosure may be employed. Further, this example is described with respect to an example health gateway 120 employing a BLE communications technique; however, any other suitable communications technique may be employed.

At block 1310, a health gateway 120 (or wireless AP 122) transmits a broadcast signal using the packet formats described above with respect to FIGS. 6A-6B and 7A-7B. The broadcast signal is configured to advertise the availability of the health gateway 120 for communication, and provides information, such as service information, including manufacturer-specific data, or connection information to enable a wireless device to determine whether the health gateway 120 provides services usable by the wireless device 110. In some examples, however, the broadcast signal may not include such information, and instead may be an advertisement packet configured to indicate the availability of the health gateway 120 for communication.

The service information may include a type of monitoring service, service provider, or customer backend that the health gateway can communicate with, or any other type of service information discussed herein. In some examples, the service information may include types of data the health gateway can process, such as blood pressure, heart rate, ECG information, blood oxygen levels, glucose levels, drug dosage or usage information, etc. Service information may also include information such as manufacturer-specific data, such as make or model of the health gateway, software version information, etc.

At block 1320, the health gateway 120 receives a response from a wireless device 110. In this example, the wireless device 110 receives the broadcast signal and determines that the health gateway 120 is suitable for communication, such as generally described above with respect to block 1230 of FIG. 12. The wireless device 110 may then transmit a message to the health gateway 120 indicating the health gateway 120 is suitable for connection, or to establish a connection with the health gateway 120.

In some examples, the health gateway 120 may receive a response from the wireless device 110 that indicates the characteristics of the wireless device 110, such as service information or manufacturer-specific data. Such information may be used at block 1330 to determine whether the wireless device 110 is suitable for connection with the health gateway 120. Such information may be provided by the wireless device 110 even if the wireless device 110 determines that the health gateway 120 is suitable for communication.

At block 1330, the health gateway 120 determines whether the wireless device 110 is suitable for connecting to the health gateway 120, such as described above with respect to FIG. 8. In this example, the health gateway 120 determines whether the wireless device 110 is suitable for connection based on received service information or manufacturer-specific data. For example, the health gateway 120 may determine whether the wireless device 110 is suitable for communication such as described above with respect to FIG. 8. In some examples, the health gateway 120 may determine whether service information or manufacturer-specific data indicates that the wireless device 110 is compatible with the health gateway 120, or is of a type of device authorized to connect to the health gateway 120.

At block 1340, the health gateway 120 establishes a communications connection with the wireless device 110. For example, the health gateway 120 may establish a BLE or WiFi connection with the wireless device 110 after determining it is suitable at block 1330.

While the method of FIG. 13 was described with respect to a health gateway 120 communicating with a wireless device 110, it should be appreciated that the method may be employed with respect to any suitable wireless AP or health gateway according to this disclosure.

Figure 14:
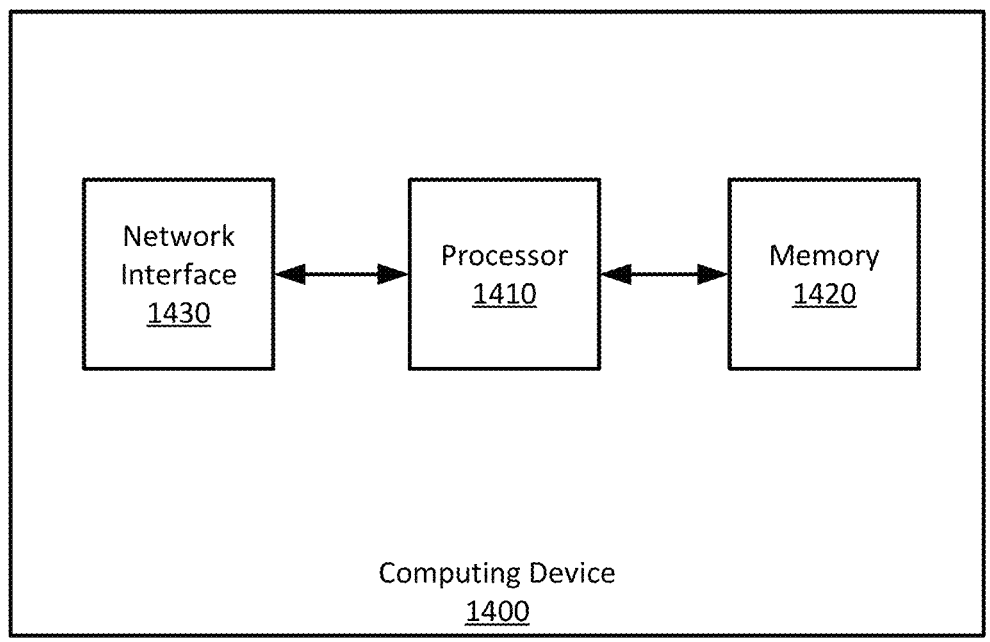
FIG. 14 shows an example computing device for dynamic provisioning of wireless devices with health gateways.

Referring now to FIG. 14, FIG. 14 shows an example computing device 1100 that may be employed with systems or methods for dynamic provisioning of wireless devices with health gateways. For example, the service provider 130 or the customer backend 140 may employ one or more example computing devices 1400 according to this disclosure.

The example computing device 1400 includes one or more processors 1410 in communication with memory 1420 and a network interface 1430. The memory 1420 may include volatile random-access memory ("RAM"), non-volatile RAM ("NVRAM"), such as a hard drive or flash memory, or a combination of RAM and NVRAM. The network interface 1430 may provide a communications interface between the computing device 1400 and one or more networks, such as the networks 150, 152 shown in FIG. 1A. In some examples, the computing device 1400 may be in communication with an external data store, such as a database server or database management system within which data obtained from one or more wireless devices 110 may be stored.

While the methods and systems herein are described in terms of software executing on various machines, the methods and systems may also be implemented as specifically-configured hardware, such as field-programmable gate array (FPGA) specifically to execute the various methods. For example, examples can be implemented in digital electronic circuitry, or in computer hardware, firmware, software, or in a combination thereof. In one example, a device may include a processor or processors. The processor comprises a computer-readable medium, such as a random access memory (RAM) coupled to the processor. The processor executes computer-executable program instructions stored in memory, such as executing one or more computer programs. Such processors may comprise a microprocessor, a digital signal processor (DSP), an application-specific integrated circuit (ASIC), field programmable gate arrays (FPGAs), and state machines. Such processors may further comprise programmable electronic devices such as PLCs, programmable interrupt controllers (PICs), programmable logic devices (PLDs), programmable read-only memories (PROMs), electronically programmable read-only memories (EPROMs or EEPROMs), or other similar devices.

Such processors may comprise, or may be in communication with, media, for example computer-readable storage media, that may store instructions that, when executed by the processor, can cause the processor to perform the steps described herein as carried out, or assisted, by a processor. Examples of computer-readable media may include, but are not limited to, an electronic, optical, magnetic, or other storage device capable of providing a processor, such as the processor in a web server, with computer-readable instructions. Other examples of media comprise, but are not limited to, a floppy disk, CD-ROM, magnetic disk, memory chip, ROM, RAM, ASIC, configured processor, all optical media, all magnetic tape or other magnetic media, or any other medium from which a computer processor can read. The processor, and the processing, described may be in one or more structures, and may be dispersed through one or more structures. The processor may comprise code for carrying out one or more of the methods (or parts of methods) described herein.

The foregoing description of some examples has been presented only for the purpose of illustration and description and is not intended to be exhaustive or to limit the disclosure to the precise forms disclosed. Numerous modifications and adaptations thereof will be apparent to those skilled in the art without departing from the spirit and scope of the disclosure.

Reference herein to an example or implementation means that a particular feature, structure, operation, or other characteristic described in connection with the example may be included in at least one implementation of the disclosure. The disclosure is not restricted to the particular examples or implementations described as such. The appearance of the phrases "in one example," "in an example," "in one implementation," or "in an implementation," or variations of the same in various places in the specification does not necessarily refer to the same example or implementation. Any particular feature, structure, operation, or other characteristic described in this specification in relation to one example or implementation may be combined with other features, structures, operations, or other characteristics described in respect of any other example or implementation.

Use herein of the word "or" is intended to cover inclusive and exclusive OR conditions. In other words, A or B or C includes any or all of the following alternative combinations as appropriate for a particular usage: A alone; B alone; C alone; A and B only; A and C only; B and C only; and A and B and C.

What is claimed is:

1. A method for dynamic provisioning of a wireless device with a health gateway, the method comprising:
   detecting, by the wireless device, a signal from the health gateway, the signal including connection information and service information, the service information comprising at least one service universally unique identifier ("service UUID"), wherein the at least one service UUID corresponds to at least one service provider or customer backend of the health gateway;
   determining, before establishing a communications connection with the health gateway, whether the health gateway is suitable based at least in part on the connection information and the service information, including the at least one service UUID, in combination with manufacturer-specific data of the wireless device, the manufacturer-specific data comprising a device model of the wireless device and a manufacturing company of the wireless device; and
   in response to determining that the health gateway is suitable, establishing a communications connection with the health gateway.

2. The method of claim 1, wherein determining whether the health gateway is suitable is based at least in part on a compatibility between a service provider or a customer backend and the wireless device, the compatibility determined using the at least one service UUID, the device model of the wireless device, and the manufacturing company of the wireless device, the health gateway in communication with the service provider or the customer backend.

3. The method of claim 1, wherein the service information comprises a type of data processed by the health gateway or health gateway manufacturer-specific data, and wherein determining whether the health gateway is suitable is further based at least in part on a type of data obtainable by the wireless device or determining that the health gateway manufacturer-specific data is compatible with the wireless device.

4. The method of claim 1, wherein determining whether the health gateway is suitable comprises determining that the health gateway is not designated as unsuitable by the wireless device.

5. The method of claim 1, wherein the signal is received from a wireless access point in communication with the health gateway.

6. The method of claim 1, wherein the wireless device comprises a medical device.

7. A wireless device comprising:
   a wireless transceiver;
   a non-transitory computer-readable medium; and
   a processor in communication with the non-transitory computer-readable medium and configured to:
      detect, using the wireless transceiver, a signal from a health gateway, the signal including connection information and service information, the service information comprising at least one service universally unique identifier ("service UUID"), wherein the at least one service UUID corresponds to at least one service provider or customer backend of the health gateway;
      determine, before establishing a communications connection with the health gateway, whether the health gateway is suitable based at least in part on the connection information and the service information, including the at least one service UUID, in combination with manufacturer-specific data of the wireless device, the manufacturer-specific data comprising a device model of the wireless device and a manufacturing company of the wireless device; and
      in response to a determination that the health gateway is suitable, establish a communications connection with the health gateway.

8. The wireless device of claim 7, wherein determining whether the health gateway is suitable is based at least in part on a compatibility between a service provider or a customer backend and the wireless device, the compatibility determined using the at least one service UUID, the device model of the wireless device, and the manufacturing company of the wireless device, the health gateway in communication with the service provider or the customer backend.

9. The wireless device of claim 7, wherein the service information comprises a type of data processed by the health gateway or health gateway manufacturer-specific data, and wherein determining whether the health gateway is suitable is further based at least in part on a type of data obtainable by the wireless device or determining that the health gateway manufacturer-specific data is compatible with the wireless device.

10. The wireless device of claim 7, wherein determining whether the health gateway is suitable comprises determining that the health gateway is not designated as unsuitable by the wireless device.

11. The wireless device of claim 7, wherein the signal is received from a wireless access point in communication with the health gateway.

12. The wireless device of claim 7, wherein the wireless device comprises a medical device.

13. A non-transitory computer-readable medium comprising processor-executable instructions for dynamic provisioning of a wireless device with a health gateway, the instructions configured to cause a processor to:
    detect, by the wireless device, a signal from the health gateway, the signal including connection information and service information, the service information comprising at least one service universally unique identifier ("service UUID"), wherein the at least one service UUID corresponds to at least one service provider or customer backend of the health gateway;
    determine, before establishing a communications connection with the health gateway, whether the health gateway is suitable based at least in part on the connection information and the service information, including the at least one service UUID, in combination with manufacturer-specific data of the wireless device, the manufacturer-specific data comprising a device model of the wireless device and a manufacturing company of the wireless device; and
    in response to a determination that the health gateway is suitable, establish a communications connection with the health gateway.

14. The non-transitory computer-readable medium of claim 13, wherein determining whether the health gateway is suitable is based at least in part on a compatibility between a service provider or a customer backend and the wireless device, the compatibility determined using the at least one service UUID, the device model of the wireless device, and the manufacturing company of the wireless device, the health gateway in communication with the service provider or the customer backend.

15. The non-transitory computer-readable medium of claim 13, wherein the service information comprises a type of data processed by the health gateway or health gateway manufacturer-specific data, and wherein determining whether the health gateway is suitable health gateway is further based at least in part on a type of data obtainable by the wireless device or determining that the health gateway manufacturer-specific data is compatible with the wireless device.

16. The non-transitory computer-readable medium of claim 13, wherein determining whether the health gateway is suitable comprises determining that the health gateway is not designated as unsuitable by the wireless device.

17. The non-transitory computer-readable medium of claim 13, wherein the signal is received from a wireless access point in communication with the health gateway.

18. The non-transitory computer-readable medium of claim 13, wherein the connection information comprises a Bluetooth Low-Energy ("BLE") passcode and the service information comprises an identity of a cloud service provider.

19. The non-transitory computer-readable medium of claim 13, wherein the wireless device comprises a medical device.

20. A method for dynamic provisioning of a wireless device with a health gateway, the method comprising:
    receiving, by the health gateway, a wireless signal from the wireless device, the wireless signal indicating information about the wireless device, the information about the wireless device comprising manufacturer-specific data of the wireless device, wherein the manufacturer-specific data of the wireless device comprises a device model of the wireless device and a manufacturing company of the wireless device;
    determining, before establishing a communications connection with the health gateway, whether the wireless device is suitable based at least in part on the information about the wireless device, including the device model of the wireless device and the manufacturing company of the wireless device, in combination with a service universally unique identifier ("service UUID") of the health gateway, wherein the service UUID corresponds to at least one service provider or customer backend of the health gateway; and
    in response to a determination that the wireless device is suitable, establishing a communications connection with the wireless device.

21. The method of claim 20, wherein:
    the wireless signal comprises an advertisement packet;
    the information about the wireless device further comprises connection and service information; and
    determining whether the wireless device is suitable is further based at least in part on the connection and service information.

22. The method of claim 20, wherein the device model comprises a model identification number of the wireless device.

23. The method of claim 20, wherein the wireless signal was transmitted with a signal strength configured to have a first transmission range.

24. The method of claim 23, further comprising, after establishing the communications connection with the wireless device, transmitting a second wireless signal to the wireless device, the second wireless signal transmitted with a signal strength configured to have a second transmission range, the second transmission range greater than the first transmission range.

25. The method of claim 20, further comprising, prior to receiving the wireless signal from the wireless device, broadcasting an advertising signal.

26. A wireless device comprising:
    a wireless transceiver;
    a non-transitory computer-readable medium; and
    a processor in communication with the non-transitory computer-readable medium and configured to:
        receive, using the wireless transceiver, a wireless signal from a second wireless device, the wireless signal indicating information about the second wireless device, the information about the second wireless device comprising manufacturer-specific data of the second wireless device, wherein the manufacturer-specific data of the second wireless device comprises a device model of the second wireless device and a manufacturing company of the second wireless device;
        determine, before establishing a communications connection with the health gateway, whether the second wireless device is suitable based at least in part on the information about the second wireless device, including the device model of the second wireless device and the manufacturing company of the second wireless device, in combination with a service universally unique identifier ("service UUID") of the wireless device, wherein the service UUID corresponds to at least one service provider or customer backend of the wireless device; and
        in response to a determination that the second wireless device is suitable, establish a communications connection with the second wireless device.

27. The wireless device of claim 26, wherein: the wireless signal comprises an advertisement packet;
    the information about the second wireless device further comprises connection and service information; and the determination of whether the second wireless device is suitable is further based at least in part on the connection and service information.

28. The wireless device of claim 26, wherein the device model comprises a model identification number of the second wireless device.

29. The wireless device of claim 26, wherein the wireless signal was transmitted with a signal strength configured to have a first transmission range.

30. The wireless device of claim 29, further comprising, after establishing the communications connection with the second wireless device, transmitting a second signal to the second wireless device, the second signal transmitted with a signal strength configured to have a second transmission range, the second transmission range greater than the first transmission range.

31. The wireless device of claim 26, further comprising, prior to receiving the wireless signal from the second wireless device, broadcasting an advertising signal.

* * * * *